US007282210B2

(12) United States Patent
Lemesre

(10) Patent No.: US 7,282,210 B2
(45) Date of Patent: Oct. 16, 2007

(54) PROCESS FOR THE IN VITRO CULTURE OF DIFFERENT STAGES OF TISSULAR PARASITES

(75) Inventor: Jean-Loup Lemesre, Saint Martin de Londres (FR)

(73) Assignee: Institut de Recherche pour de Developpement (IRD), Paris Cedex (FR)

( * ) Notice: Subject to any disclaimer, the term of this patent is extended or adjusted under 35 U.S.C. 154(b) by 0 days.

(21) Appl. No.: 10/190,607

(22) Filed: Jul. 9, 2002

(65) Prior Publication Data

US 2003/0068690 A1    Apr. 10, 2003

Related U.S. Application Data

(62) Division of application No. 08/549,677, filed as application No. PCT/FR94/00577 on May 13, 1994, now Pat. No. 6,458,581.

(30) Foreign Application Priority Data

May 13, 1993   (FR) .................................. 93 05779

(51) Int. Cl.
*A61K 39/00* (2006.01)
*A61K 39/002* (2006.01)
*C07K 1/00* (2006.01)

(52) U.S. Cl. ............................ 424/265.1; 424/266.1; 424/269.1; 530/350

(58) Field of Classification Search ............ 424/265.1, 424/269.1, 266.1; 530/350
See application file for complete search history.

(56) References Cited

U.S. PATENT DOCUMENTS

| 3,911,097 A | 10/1975 | Hanson |
| 3,993,743 A | 11/1976 | Hanson |
| 4,687,666 A | 8/1987 | O'Daly |
| 5,719,263 A * | 2/1998 | Reed ........................ 530/324 |

FOREIGN PATENT DOCUMENTS

| EP | 0 420 635 | 4/1991 |
| WO | 83/01785 | 5/1983 |
| WO | 93/03167 | 2/1993 |

OTHER PUBLICATIONS

Lemesre et al, "Requirements of defined cultivation conditions for standard growth of Leishmania promastigotes in vitro". Acta Tropica 45(2):99-108 (1988).
Joshi et al, "Cloning and characterization of differentially expressed genes from in vitro-grown amastigotes' of leishmania donovani". Molecular and Biochemical Parasitology 58(2):345-354 (1993).
Hart et al, "Transformation in vitro of Leishmania mexicana amastigotes to promastigotes: nutritional requirements and the effect of drugs". Parasitology 33:529-541 (1981).
Kweider et al, "Development of metacic Leismania pasties is associated in the increasing expression GP55.e major surface antigen". Parasite Immunol 11:197-209 (1989).
O'Daly et al, "Differential growth requirements of several Leisnmania spp. in chemically defined culture media". Acta Tropica 45:109-126 (1988).
De Castro et al, "Trypanosoma cruzi: Adrenergic Modulation of Cyclic AMP Role in Proliferation and Differentiation of Amastigotes In Vitro". Experimental Parasitology 54:368-375 (1987).
Velasco et al, "A Survey of Culture Media of Trypanosoma cruzi Amastigote Forms From Infected Vero Cells". Chemosohere 19(10/11):1743-1748 (1989).
Velasco et al, "In Vitro Survival of Amastigote Forms of Trypanosoma cruz: In Media Conditioned By Vero Cells", Chemosohere 21(1-2):253-268 (1990).
Bates et al. Parastiology 105(2):193-202 (1992).
Bates et al. ParastiologyToday 9(4):143-146 (1993).
Chaudhuri et al. Indian J. Med. Res. 84:457-460 (1986).
Childs et al. Int. J. Parasitol. 8(4):255-258 (1978).
Hirumi et al. Parasitol. 102(2):225-236 (1991).
Hirumi et al. J. Parasitol. 75(6):985-989.
Lima et al. J. Protozool. 35(1):108-110 (1988).
Lemesre et al, "Protection against experimental visceral leishmaniasis infection in dogs immunized with purified excreted secreted antigens of *Leishmania infantum* promastigotes", Vaccine 23 (2005) 2825-2840.

* cited by examiner

*Primary Examiner*—Mark Navarro
(74) *Attorney, Agent, or Firm*—Nixon & Vanderhye P.C.

(57) ABSTRACT

The present invention provides a method for carrying out in vitro the complete developmental sequence culture of tissular parasites, which includes culturing the parasites in a totally defined culture medium which is an axenic . . . monophasic liquid culture medium, free of serum and free of serum-derived or cell-derived macromolecules, proteins and peptides. For obtaining amastigote forms, this medium is buffered at a pH of 5.5 to 6.5 and has an osmolarity of at least 400 milliosmoles/kg of liquid. For obtaining promastigote forms, the medium is buffered at a pH of 7 to 7.5 and has an osmolarity of at least 300 milliosmoles/kg liquid. Application to the in vitro culture of different stages of tissular parasites such as *Leishmania, T. cruzi*, and hamatoprotozoa is also provided.

14 Claims, 12 Drawing Sheets

PROCESS FOR THE IN VITRO CULTURE OF DIFFERENT STAGES OF TISSULAR PARASITES

Figure 1A:
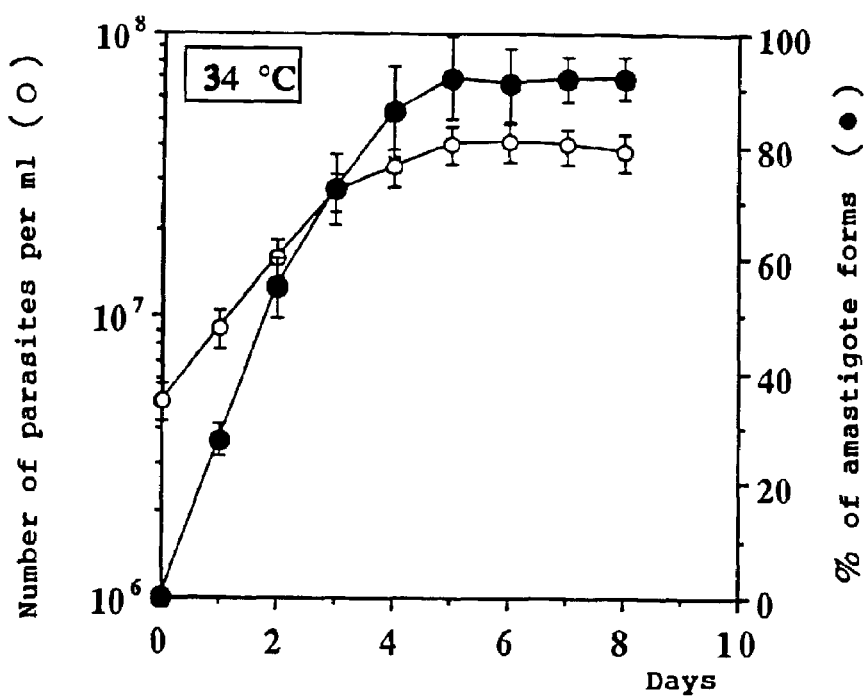

This application is a divisional of application Ser. No. 08/549,677, filed Nov. 9, 1995, now U.S. Pat. No. 6,458,581; which is a national phase of Appln. No. PCT/FR94/00577, filed May 13, 1994; the entire contents of which are hereby incorporated by reference in this application.

A subject of the invention relates to a process for the in vitro culture of different stages of the developmental cycle of a parasite. It also relates to the parasitic forms obtained and their biological uses.

By culture is meant, in the description which follows and the claims, both the adaptation of the parasitic form by successive passages in a given medium, and complete differentiation when it occurs for the adaptation and the culture itself of the parasitic form.

It is known that parasites constitute a real plague causing, by the intermediary of vectors, the infection of millions of people and animals.

Thus, leishmaniases, which are widespread throughout the world, are caused by protozoa of the *Leishmania* genus which are usually transmitted by a sand fly, Phlebotomus. Leishmaniases of the Old World and those of the New World are usually distinguished according to their geographical localization. They have very diverse clinical forms which differ significantly by their seriousness and their effect on health. Cutaneous, mucocutaneous (attacking nasal, buccal mucous membrane and those of the ears) and visceral leishmaniases are distinguished.

As another parasite having a devastating effect, there can also be mentioned *Trypanosoma cruzi*, responsible for Chagas' disease. In South America, it causes the infection of millions of people. Over 150 species of wild and domestic animals can be counted which can serve as hosts to the parasite which is transmitted to man by a bug, namely a *Triatoma*, which feeds on blood.

The infection can pass unnoticed for several years until the trypanosomas attack the nervous system, the heart or the digestive system.

The development cycle of many parasites includes various parasitic stages. That of *Leishmania*, for example, includes two stages having important differences at the structural, morphological, biochemical, immunological and physiological level, namely in a vector insect, a flagellated form, called promastigote, which multiplies by scissiparity before acquiring its infectious form, for the mammalian host, also called metacyclic, in a mammalian host, a non-flagellated stage, called amastigote, which exclusively parasitizes mononuclear phagocyte cells.

The differentiation into amastigotes occurs after attachment and penetration of the promastigotes into the monocytes. But only the amastigote forms persist and multiply inside the phagolysosome of the macrophages of the infected host.

In *T. cruzi*, this cycle includes three different parasitic stages, an epimastigote form, multiplication form of the vector insect, and the amastigote and trypomastigote forms, which are present in the infected host.

At present, most of the research carried out on the diagnosis of these parasitoses and the development of vaccines is conducted on the promastigote form whose production in culture is easy and quick.

Now, the only form present in the infected host is the amastigote form which, by persisting throughout the infection, triggers the immune response and participates in the development of the pathology. The danger of systematically extrapolating the experimental results obtained with the cultured promastigote forms within the scope of immuno-prophylactic, diagnostic or therapeutic studies aimed at the amastigote forms will be well understood.

In order to respond to this problem, various authors have been interested in obtaining amastigote forms. Thus the obtaining of amastigotes from tissues of experimentally infected animals or from cultures of infected macrophages have been reported. But this involves long and tedious isolation methods, which moreover lead to a limited number of parasites being obtained, which are often degenerated and which are incapable of multiplying and of surviving for longer than 2 to 3 days.

Furthermore, such amastigote forms are contaminated with cells, fragments and molecules derived from the macrophages, tissues or plasma of the host, designated hereafter by "cellular contaminants", limiting or making impossible the realization of many studies.

Culturing processes under axenic conditions, that is to say in the absence of any cellular contaminant, have been proposed for some species of *Leishmania* and for *T. cruzi*, but they do not allow an abundant and continual source of amastigote forms to be made available, and do not appear to be generally applicable to a large number of species and to different germs.

An aim of the invention is to resolve the above disadvantages and to provide more satisfactory experimental models by producing the desired parasitic stages in specific culture media, of totally defined simplified composition.

The invention relates in particular to providing a process generally applicable to a large number of species of a given parasite, allowing homogeneous populations of a given parasitic stage to be produced in a continuous manner and in unlimited quantities.

It relates more particularly to a process allowing these stages to be obtained in a form which is free from any cellular and seric contaminant, having the characteristic of not containing any macromolecules. By macromolecules is meant, in the description and the claims which follow, non-dialyzable molecules with a cut-off threshold of 3 kDa, that is to say having an apparent molecular weight of greater than 3 kDa (for example seric protein such as albumin).

It also relates to the in vitro production of the complete development cycle of parasites under axenic and aseric conditions.

According to another aspect, the invention relates to the new parasitic forms obtained, corresponding to the different stages of the parasitic cycle and, for each stage, to the different phases of their growth.

According to another aspect, the invention relates to the applications of the parasitic stages obtained and of the products produced or isolated from these stages, in particular in the domain of the diagnosis of parasitoses, immuno-prophylaxis and screening of drug activities.

The process according to the invention, for the in vitro culture of different stages of tissular parasites, such as *Leishmania, T. cruzi*, or also hematoprotozoa is characterized in that it is carried out in an axenic and aseric, liquid single-phase culture medium, free from macromolecules (non-dialyzable at a cut-off threshold of 3 kDa) and that for obtaining amastigote forms, this medium is buffered at a pH of 5.5 to 6.5 and has an osmolarity of at least 400 milliosmoles/kg of liquid, and in particular from 400 to 550 milliosmoles/kg of liquid, or that, for obtaining promastigote forms, this medium is buffered at a pH of 7 to 7.5 and has an osmolarity of at least 300 milliosmoles/kg of liquid, and in particular from 300 to 380 milliosmoles/kg of liquid.

The pH value of these media, within the range indicated above, ensures that the culture conditions are strictly controlled.

In the case of the culture of amastigotes, when the pH is greater than 6.5, a tendency towards the retransformation of the amastigotes into promastigotes is in fact noted and when it is less than 5.5, a poor growth is observed.

According to a preferred method of the invention, for obtaining amastigote forms, a culture medium is used containing a base medium, produced essentially from:
  at least one culture medium for insect cells which has added to it inorganic salts, of Hanks' salts type,
  products which are sources of amino acids, such as L-glutamine and soja bean extracts,
  sugars, such as D-glucose.

As soja bean extact, there can advantageously be used that marketed under Soja tryptocasein $^R$.

The culture medium for insect cells is advantageously the medium 199 H marketed by GIBCO BRL.

Different compositions of this 199 H $^R$ medium are given in the GIBCO BRL catalogue page 48, 1992 edition.

A specially preferred composition for the production of base media carries the reference 042-01181 on page 48 of this catalogue, 1992 edition. The 199H M medium is more especially used, to which $NaHCO_3$ and L-glutamine are added.

This medium, to which the above compounds are added, is advantageously buffered, for example with a buffer such as HEPES.

A preferred composition of the base medium contains several culture media for insect cells.

A base medium of this type results from the addition to the 199 H medium as marketed by GIBCO BRL, to which the compounds mentioned above have been added, of another medium such as the modified 199 H medium as marketed by Flow. A composition of this medium is given in the Flow Laboratories catalogue, 1992 under the reference 14230-54. Before adding it to the initial preparation, this latter modified 199 H medium is subjected to a thermal treatment.

The base media defined above are new and, as such, are also a subject of the invention. They can be stored for several months at −20° C.

In order to avoid oxidation of the parasitic stages, this base medium has added to it, at the time of use, anti-oxidizing agents such as hemin, which also has the advantage of constituting a source of iron and agents with a reducing effect such as reduced glutathionee. Vitamins are also advantageously added. A suitable mixture of vitamins includes biotin, calcium D pantothenate, choline chloride, folic acid, inositol, nicotinamide, para-aminobenzoic acid, pyridoxine hydrochloride, riboflavin, thiamine hydrochloride, vitamin B12, some of which are used and advantageously all of which are used.

The resultant culture media are advantageously characterized in that they are free from nucleotides as additives. They can be stored at +4° C. for about two weeks without alteration to their properties.

The use of the resultant culture media, as illustrated by the examples given hereafter, allows amastigote forms to be produced which are capable of mass multiplication in vitro, in a continuous manner.

The axenic and aseric media have the advantage of being free from all macromolecules and in particular from those present in foetal calf serum and/or originating from the host cells, which can mask other constituents (seric and cellular proteins).

These media are particularly suitable for the amastigote forms of tissular protozoa, such as cutaneous or muco-cutaneous or visceral *Leishmanias*, or various clones of *T. cruzi*, or also *Plasmodium* or *Babesia*.

As species of *Leishmania*, there can be mentioned *L. mexicana, L. amazonensis*, and *L. braziliensis* or also *L. major, L. guyanensis* and *L. panamensis*. Other preferred culture media, particularly suitable for the culture of the amastigote forms of visceral *Leishmania*, such as *L. donovani, L. infantun* and *L. chagasi*, contain, in addition, sulphurous compounds. These are in particular sulphurated amino acids, such as cysteine, and notably the L form, and/or nutritive products such as bathocuproine sulphonic acid.

For the differentiation of promastigote forms into amastigote forms, in the case of *Leishmania*, the cellular culture medium represents, relative to the final medium, about 8% to 15% (V/V), notably of the order of 10%, the amino acids, or products which are sources of these amino acids, such as soja trypto casein $^R$ and L-glutamine, are present at a rate of about 4% to 8% (W/V), notably about 5% to 6%, the supply of sugar, notably as glucose, is advantageously carried out at a rate of about 2% to 4% (W/V), notably 2% to 3%, the anti-oxidizing agents such as hemin, at a rate of 0.0002% to 0.0015% (W/V), notably of the order of 0.0005%, and glutathione at a rate of 0.01% to 0.05%, notably of the order of 0.025% and the vitamin solution (100×) at a rate of 1% to 5% (V/V), notably of the order of 2%.

The sulphurous compounds, when they are used, in particular L-cysteine, are used at a rate of about 0.25 to 0.50% (W/V), notably of the order of 0.3%, and bathocuproine sulphonic acid is used at a rate of about 0.004 to 0.008% (W/V), notably of the order of 0.005%.

For the culture of the promastigote stages, a culture medium is advantageously used which is produced from a medium suitable for cell culture, such as RPMI 1640 medium, to which are added amino acids such as L-glutamine and a buffer to adjust the pH to a value of 7 to 7.5, this medium also having added to it another medium suitable for cell culture, in particular 199H M medium, containing inorganic salts such as Hanks' salts, and anti-oxidizing agents, such as hemin.

This medium is therefore free from any seric contaminant and contains no macromolecule as proved by 10% polyacrylamide gel analysis.

The 199H M medium is used at a rate of about at least 2% (V/V), notably about 2 to 10% and bovine hemin is used at a rate of 0.0001 to 0.0015% (W/V), notably of the order of 0.0005%.

The simplicity of preparation of such a medium from products which are already being marketed will be observed. Moreover the absence of serum advantageously produces an inexpensive product.

In accordance with the invention, these culture media are used in a process for the continuous mass production of parasitic forms.

For the adaptation and continuous culture in vitro of amastigote forms, a suitable culture medium as defined above is inoculated with promastigotes at the end of the exponential phase, at a rate of $10^6$ to $10^7$ promastigotes/ml of medium.

The conditions for carrying out the adaptation and culture are advantageously chosen in such a way as to ensure a total transformation of the parasites in a reproducible manner.

The adaptation, then the culture, are carried out at temperatures of the order of 28° C. to 36° C., and notably around 32° C. at a pH of 5.5 to 6.5. Usually a transformation of the promastigote forms into amastigote forms in excess of 90% is observed in 6 to 7 days. This transformation is for example total in 4 days for the *Leishmania*, after a number of passages which varies according to the species studied and which generally corresponds to 3 to 9 subcultures, and which decreases when the incubation temperature increases.

For the adaptation and continuous culture in vitro of so-called primary culture or short-term promastigote forms of parasites, such as *Leishmania*, directly obtained from the amastigote forms, inoculation with the amastigote forms as obtained above is carried out, at a rate of $10^6$ to $10^7$ amastigote forms/ml of medium. Amastigote forms at the end of the exponential phase are advantageously used. The culture is carried out at a temperature close to ambient temperature but preferably not exceeding 28° C. at a pH of 7 to 7.5 in a culture medium as defined above for the development of promastigote forms.

When the use intended for these parasitic stages does not require both axenic and aseric conditions, without the presence of macromolecules, to be used, it is possible within the scope of the invention to carry out the culture in a purely axenic medium, therefore in the presence of serum and also in the presence of macromolecules. For example RPMI medium which has foetal calf serum added to it can be used.

The short-term promastigote forms thus obtained can be used in the inoculation stage mentioned above for the purposes of the differentiation into amastigotes.

The transformation is very rapid and total, for example *Leishmania* in 4 days, after 2 to 5 subcultures, according to the species.

The implementation of the provisions of the invention allows standardized and reproducible cultures of the various forms corresponding to the various parasitic stages to be obtained, which are free from any cellular contaminant and from macromolecules and capable of multiplying in vitro.

The provisions which precede have been described more particularly relative to the promastigote forms and the amastigote forms of *Leishmania*, whether cutaneous, mucocutaneous or also visceral *Leishmania*, but also apply to the parasitic stages of *T. cruzi* or other hematoprotozoa such as *Plasmodium* and *Babesia*.

These cultures can be kept for several months, even several years for many species, in particular for *Leishmania*, whether they are cutaneous, mucocutaneous or visceral, or for *T. cruzi*.

The parasitic stages are capable of undergoing long-term cultivation, that is to say over more than 50 passages in in vitro cultures, and short-term cultivation, that is to say recently transformed from promastigote forms or from amastigote forms (earlier form of the cycle) of less than 10 passages.

The invention also supplies the means for producing a complete parasitic cycle in vitro. It will advantageously be noted that this complete cycle can be carried out in less than 15 days.

An embodiment of a process, according to the invention, for the production of stages corresponding to the developmental cycle of a parasite such as *Leishmania* is characterized in that it is used under the axenic and aseric conditions defined above, in the absence of macromolecules and in that it comprises:

inoculation of a suitable culture medium, as defined above, with short-term or long-term promastigote forms, so as to obtain the differentiation into amastigote forms, recovery of the amastigote forms produced, their inoculation and their culture as indicated above so as to obtain the differentiation into promastigote forms, the cycle being repeated in its entirety, or partially, if desired, and indefinitely.

According to another embodiment, the short-term forms are cultivated under purely axenic conditions, or axenic and aseric conditions in the presence of macromolecules.

Via the process of the invention, it is therefore possible to obtain in vitro the various parasitic stages much more quickly and easily than by the in vivo techniques currently used which involve experimental infections which are sometimes difficult to bring about. These amastigote or promastigote parasitic forms are free from any cellular contaminant and are capable of multiplying in vitro. Thus means are available which allow the abundant, and even unlimited, obtaining of the parasitic stages recently, or not, differentiated from the earlier stage, in particular of *Leishmania* and those of *T. cruzi* (epimastigotes, metacyclic and bloodstream trypomastigotes and amastigotes).

Also a subject of the invention is the parasitic forms of the developmental cycle of a tissular protozoan, such as *Leishmania* or *T. cruzi*, as obtained by implementing the culture process defined above.

These forms are characterized in that:

they are free from cellular contaminants, in particular tissular macrophage and plasmatic contaminants accompanying the intracellular parasitic forms isolated from cell cultures or from tissues of experimentally-infected animals, as well as any seric contaminant, while being endowed with infective power in vitro and in vivo as observed on the intracellular forms when these are habitually infective, and their morphological, biochemical and immunological characteristics, they are presented in the form of a homogeneous population relative to the age in culture and the state of differentiation for a given stage of the developmental cycle, this population, originating from a standardized culture, being capable of multiplying in vitro in a continuous manner.

The amastigote forms are particularly preferred given that they correspond to the forms developed during infection in man or animals.

These amastigote forms are also characterized in that they possess an enzymatic activity, more particularly a peptidase activity which is qualitatively more complex than those of the promastigotes, and quantitatively different, more particularly at the level of the cysteine-protease activities, as set out in the examples.

The invention relates more particularly to the amastigote forms of both anthroponotic and zoonotic, or anthropozoonotic *Leishmania*.

They can be the amastigote forms of cutaneous or mucocutaneous *Leishmania*. Amongst these, there can be mentioned *L. mexicana*, *L. amazonensis*, *L. braziliensis*, *L. cuyanensis* and *L. panamensis*. They can also be the amastigotes of visceral *Leishmania* such as *L. chagasi*, *L. donovani* or *L. infantum*.

Other amastigote forms according to the invention are those of various clones of *T. cruzi*.

The invention also relates to the short-term promastigote forms as defined above.

They can be populations directly transformed from amastigote forms which have an infective power similar to that of promastigotes recently isolated from an infected host.

Each of the parasitic stages, promastigote or amastigote, has different growth phases during multiplication in vitro, namely a latent phase, and exponential phase and a static stationary phase which correspond to the preparation of the division, to an intense multiplication, then to a non-division stage respectively.

The invention advantageously allows forms corresponding to one of these phases to be obtained in a targeted manner and their properties and specific biochemical characteristics to be studied.

These forms are characterized in that they are free from cellular and seric contaminants, as well as molecules non-dialyzable at a cut-off threshold of 3 kDa.

They are therefore populations defined according to a well-determined phase of their growth.

The corresponding amastigote or short-term promastigote forms are particularly preferred.

The invention also relates to the total polypeptide extracts of these parasitic forms as obtained by lysis of the cells and recovery of the soluble or insoluble products. These extracts are also called total antigenic extracts in the examples. By these expressions "total polypeptide extracts" or "total antigenic extracts" is meant the products as obtained by lysis of the parasitic forms, whether they are of protein, lipid or saccharide nature.

They can be in particular total polypeptide extracts of short-term promastigote forms and quite particularly total polypeptide extracts of amastigote forms at different stages of their growth in vitro.

These extracts are characterized by their peptide profile as revealed in a standard manner using SDS-PAGE polyacrylamide gel, under reducing condition or not, or on polyacrylamide gel under non-denaturing condition, as described in the examples for certain species of as *Leishmania*.

The invention also relates to the antigenic, protein, glucide or lipid fractions and determinants eluted or isolated from fractions of these extracts.

The antigenic fractions and determinants of these extracts recognized, according to an antigen-antibody type reaction, by sera of animals immunized with the total polypeptide extracts or sera of natural or experimental infections are particularly preferred with regard to the immunological applications which are a subject of the invention, and in particular the basic specific antigenic fractions and determinants.

Products of this type correspond to the antigens expressed on the surface of the amastigote forms and to the somatic antigens present at the level of the flagellar pocket or of vacuolar type as revealed by immunofluorescence techniques.

The purified or semi-purified molecules and the solutions specifically enriched with one or more of these molecules also come within the scope of the invention, originating from natural lyses.

Other products which are of great interest with regard to the biological applications according to the invention correspond to the excretion antigens as obtained from the culture supernatants conditioned by the promastigote forms or by the amastigote forms cultivated under the axenic and aseric conditions of the invention, originating from natural lyses.

The same goes for the differentiation antigens secreted during differentiation according to the process of the invention of the promastigote forms into amastigote forms and that of the amastigote forms into promastigote forms (during the in vitro production of the cycle).

These antigenic products are recovered from the supernatants by simple concentration and dialysis. These supernatants therefore constitute a pre-enriched purified source of antigenic products.

The invention also relates to the immunization sera as obtained after administration of the antigenic extracts, fractions and molecules defined above according to the usual techniques, and the antibodies recovered from these sera.

It also relates to the infection sera obtained by the infection of animals with the infectious amastigote forms.

The antibody content of these sera varies according to the phase of the parasitic stage and is higher against the stationary phase of the amastigote forms.

The antibodies of the invention are characterized in that they recognize the specific peptides of amastigote or promastigote parasitic forms by producing an antigen-antibody type reaction.

Such antibodies include those only specifically recognizing the antigens of an amastigote or promastigote parasitic form, belonging to a homologous species, that is to say to the same species as that used for obtaining them, the recognized form being that against which they have been formed.

They can be for example antibodies formed against an amastigote form of *Leishmania* of a given species and which only specifically recognize the antigenic peptides of the amastigote forms of this species of *Leishmania*.

The antibodies of the invention also include those which in addition have a poor recognition of the other parasitic form of the species considered.

There can be mentioned for example the anti-amastigote antibodies recognizing, to a lesser degree, antigens of the promastigote forms of the same species.

Other antibodies also of the invention are in addition capable of recognizing, but to a lesser degree, the parasitic forms of a heterologous species, or of another genus such as *T. cruzi*. Antibodies of this type correspond for example to anti-amastigote antibodies of a species of *Leishmania* recognizing amastigote peptides of another species of *Leishmania*.

According to another aspect, the invention relates to the monoclonal antibodies as advantageously obtained according to the standard techniques of fusion of a cell line with the spleen or ganglion lymphocytes of an animal immunized by injection with a total peptide extract, an antigenic fraction or molecule as defined above by screening the supernatants of the hybridomas obtained, for example according to the ELISA or IFI technique so as to reveal the antibodies directed specifically against a parasitic form of a species, as well as the clones of hybridomas secreting these monoclonal antibodies.

These antibodies constitute tools for selectively separating or isolating specific antigens of species or of stages from a medium containing them and in particular from the total polypeptide extracts mentioned above by immuno-affinity techniques.

The reaction of the above immunosera with antigenic fractions and molecules originating from a given phase of the development of the parasitic form allows the identification and isolation of the specific antigens of this stage.

The possibility of the mass production, due to the invention, of the cultured amastigote forms makes it possible to extract the total and messenger RNA's and, from these, to create a cDNA library.

According to another aspect, the invention therefore relates to the total RNA's as recovered from parasitic cultures of amastigotes or promastigotes, and the corresponding m-RNA's and cDNA's.

By comparison with a cDNA library of corresponding promastigote forms, specific peptides of a given parasitic stage are then revealed and their synthesis is proceeded with if appropriate by genetic engineering.

The obtaining, in accordance with the invention, of in vitro and in vivo infecting extracellular amastigote forms, having morphological, biological and biochemical characteristics similar to those of the intracellular amastigote forms, opens up new and numerous applications in the domains of research and industry.

The parasitic forms of the invention are thus particularly useful as experimental models for carrying out a first, screening in vitro of products which can be active for them in vivo.

The screening process of the invention comprises:
putting the parasitic forms, more especially the amastigote forms as cultivated under axenic conditions and notably aseric conditions, and the promastigote forms as cultivated in a completely defined medium, in contact with the products to be tested,
incorporation of nucleotides or amino acids labelled with a radioactive group, for example tritiated thymidine, in order to determine the activity of the products to be tested, or the carrying out of viability tests using for example a tetrazolium salt such as MTT.

In the stage of putting in contact, the parasitic forms are used at concentrations of $10^6$ parasite/ml and the activity of the medicaments is studied at increasing concentrations.

The products to be tested can advantageously be labelled, for example with a radioactive group, to determine the action mechanisms and the flow of the drugs.

Thus the invention provides a model allowing, if desired, the comparison of the in vitro activity of medicaments on the promastigote form and on the amastigote form at different phases of their growth for a given parasite, and the testing of this activity on the actual form which is found in the host.

It allows improved characterization of the medicamentous activity by revealing either a lytic effect (leishmanicidal or trypanocidal), or an inhibitory effect on the multiplication (leishmaniostatic or trypanostatic) of the product.

The use of these parasitic forms as experimental models also allows the chemical resistance of the parasitoses to be studied.

In fact it is known that at present the resistance to medicaments constitutes a significant problem. Study of the mechanisms producing this resistance, which can easily be achieved using the models of the invention, is therefore of great interest.

The invention also relates to a kit for screening products which can be used for the treatment of parasitoses, more especially *Leishmania* or Chagas' disease.

This kit comprises a support such as a multi-well plate containing the parasitic forms on which is it desired to test the activity of the product to be studied, some of these forms being used as controls, and reagents to determine the medicamentous activity of the product on the parasitic forms.

As indicated above, studies carried out up to now have not allowed parasitoses to be satisfactorily identified.

In man, or in animals and particularly in dogs, the diagnosis of leishmaniasis for example is most often determined either by isolating the parasite and identifying it (parasitological examination), or by detecting (specific circulating) antibodies in the serum (immunoserological tests).

The industrial culture of the amastigote forms under axenic or aseric conditions and in the absence of macromolecules makes available an abundant source of useful diagnostic tools.

In this way they allow the early detection, with a high degree of sensitivity and a high specificity, of circulating antibodies directed against the parasites.

The invention therefore relates to a method for the diagnosis of a parasitosis in man or animals, more especially of an infection caused by *Leishmania* or *T. cruzi*, or for their detection and identification in the vector insect, characterized in that it comprises:
putting a biological sample originating from the patient or the animal to be examined in contact with an amastigote form from an axenic and aseric culture or a promastigote form from an aseric culture as defined above, or a total polypeptide extract of these amastigote or promastigote forms, or one or more antigens specific for this extract, purified or semi-purified,
detection of the immunological complex.

The biological sample is more particularly a biological fluid such as blood, serum or urine.

When a purified or semi-purified antigen of a whole parasite is used, it is immobilized on a support.

Latex beads, ELISA plates or fluorescence slides are for example used.

The reaction can be revealed directly by macroscopic agglutination in the direct or indirect agglutination test by reacting a conjugated antibody with fluorescein (indirect immunofluorescence technique) or with an enzyme such as peroxidase or alkaline phosphatase (ELISA tests).

A positive reaction therefore allows the presence of antibodies circulating in the patient or animal examined to be diagnosed.

The invention also relates to a kit for implementing a method for diagnosing a parasitosis, as defined above, in man or in animals.

This kit is characterized in that it comprises:
the antigenic reagents in immobilized form, namely the amastigote forms from axenic culture or axenic and aseric culture or the promastigote forms of defined culture, the total polypeptide extracts obtained from these forms or the antigens specific for these extracts with, if appropriate,
a positive control, constituted by a serum of known titer, a negative control, as well as
the buffers and reagents which can be used for revealing the immunological reaction.

The detection of circulating anti-parasite antibodies in a patient or an animal can be carried out by putting in competition with the antibody of the sample, a specific antibody of the antigen, in particular a monoclonal antibody. The antibody advantageously contains a label, for example a radioactive or enzymatic group.

As a variant, the diagnostic method is based on revealing the presence of the antigenic determinants of the parasitic forms (detection of circulating antigens).

In this variant, the biological sample originating from the man or animal is put in contact with specific antibodies directed against the antigens of the parasitic form, or fragments of these antibodies.

The detection of the immunological reaction is carried out for example using the same antibody but labelled.

It is useful to note that the possibility provided by the invention of detecting circulating antigens, that is to say those which appear rapidly in the infected patient, allows early diagnosis of the disease to be carried out.

Antibodies directed against the promastigote or amastigote forms are used, in particular monoclonal antibodies, these forms originating from parasites of different species of *Leishmania* such as *L. infantum* or *T. cruzi*.

A corresponding diagnostic kit comprises:
an appropriate solid phase serving as support for the immunological reaction, such as a microtitration plate,
a preparation of antibodies according to the invention as defined above, or of fragments of these antibodies, immobilized on a support,
a positive control, constituted by a serum of known titer,
a negative control, as well as
the buffers and reagents which can be used to carry out the immunological reaction and in particular the labelled homologous antibody.

According to another aspect, the diagnostic tools of the invention allow a differential diagnosis to be carried out between several parasitoses.

In fact both in man and in animals, for example rodents, cross reactions between *T. cruzi, T. rangeli* (trypanosome non-pathogenic to man) and visceral or cutaneous *Leishmania* are observed.

The study of the parasitic forms of the invention, of the total polypeptide extracts and of the specific antigens defined above has revealed their strong immunogenic properties.

The invention therefore also relates to their use as protective agents vis-á-vis parasitoses, more especially leishmaniases and Chagas' disease.

The vaccine compositions of the invention are characterized in that they are developed from amastigote forms or promastigote forms from axenic and aseric culture, in the absence of macromolecules, as defined above, at different phases of their growth, or from their constituents, in combination with a vehicle and/or an administration adjuvant.

The constituents of the amastigote or promastigote forms in question include the total polypeptide extracts obtained by lysis of these parasitic forms. They also include the antigenic fractions and the specific protective antigens isolated from the parasitic forms, but also from the culture supernatants conditioned by the parasites when they are cultivated in completely defined media.

The administration of these protection agents to man or animals allows them to be given an overall immunity against the parasitoses in which they occur in the natural infection process.

Their advantageous effect was especially revealed at the level of the immune response to cell mediation favouring the stimulation of the T lymphocytes secreting interleukin 2, and gamma interferon ($TH_1$) or inhibiting the activation of the T cells secreting interleukins 4 and 5 ($TH_2$).

These protection agents are advantageously in lyophilized form.

In the case of total polypeptide extracts, the vaccine compositions are administered by subcutaneous route at a rate of 100 to 1000 µg in man and 100 to 500 µg in dogs in the presence of adjuvants such as muramyldipeptide or saponin or in the presence of cytokine such as gamma interferon.

The excretion-secretion antigens of the culture supernatants metabolized by the amastigote forms of the invention offer an original strategy in the development of vaccines against parasitic diseases.

Their use for producing vaccines against canine or human visceral leishmaniases (*L. intantum* and *L. chagasi*) can in particular be emphasized. In fact they advantageously correspond to the forms present in the infected host.

The various experiments carried out have allowed their immunogenic properties and their protective effect for man or animals to be revealed.

To prepare vaccines from the said antigens, or exoantigens, one uses the dialyzed concentrated supernatants of amastigote cultures, or the cultures themselves containing the parasites and the supernatants, the parasites being killed for example by thermal treatment, or extracts or these solutions.

These products are used with adjuvants such as MDP or cytokines, such as gamma interferon.

A long-term or short-term immunization protocol can be used. The long-term protocol is for example carried out by injection of the vaccine preparation every three weeks, on days d=0, d=21 and d=42. For a short-term protocol, for example, two injections are given with a two week interval.

After the virulence test, for animals, it is verified that the hypersensitivity immunity to cell mediation has indeed been induced towards the activation of the TH1 cells secreting interleukin 2 and gamma interferon.

These analyses can also be carried out for man at the end of the immunization.

Other characteristics and advantages of the invention are reported in the examples which follow.

Figure 1B:
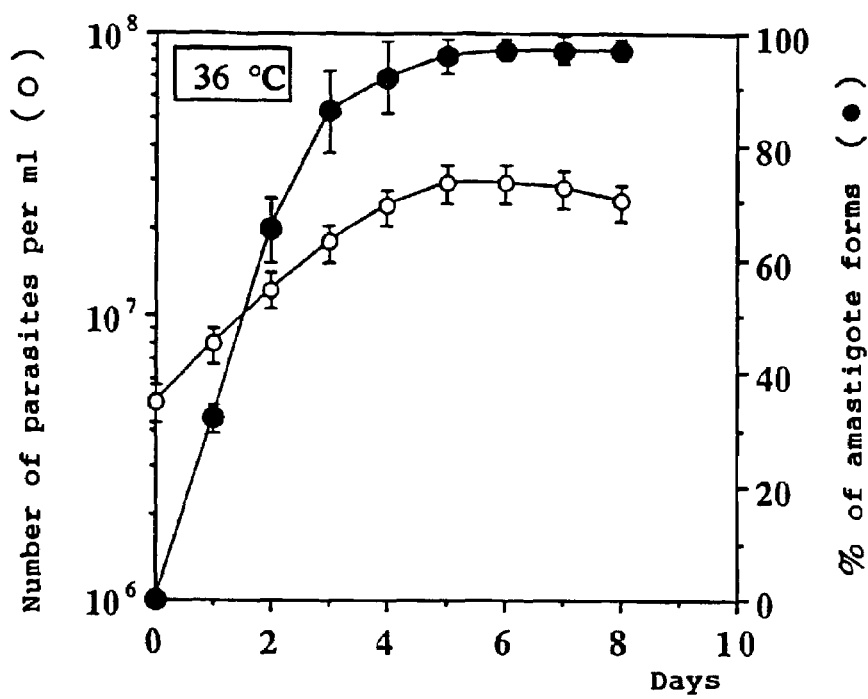
Figure 2:
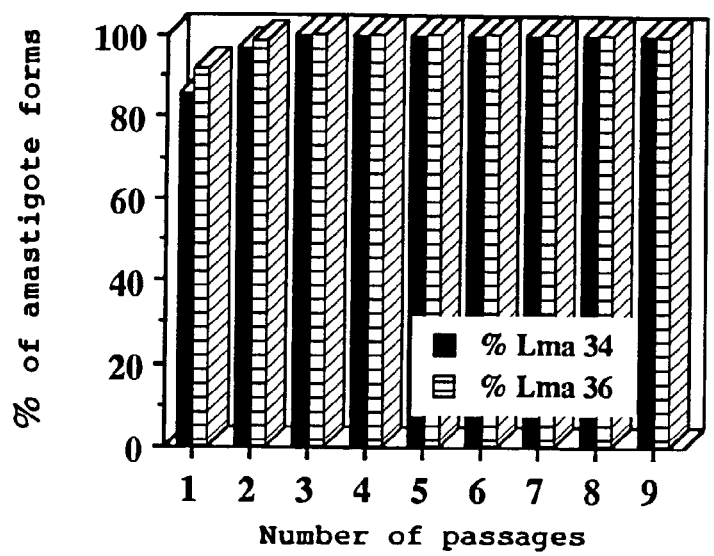
Figure 3A:
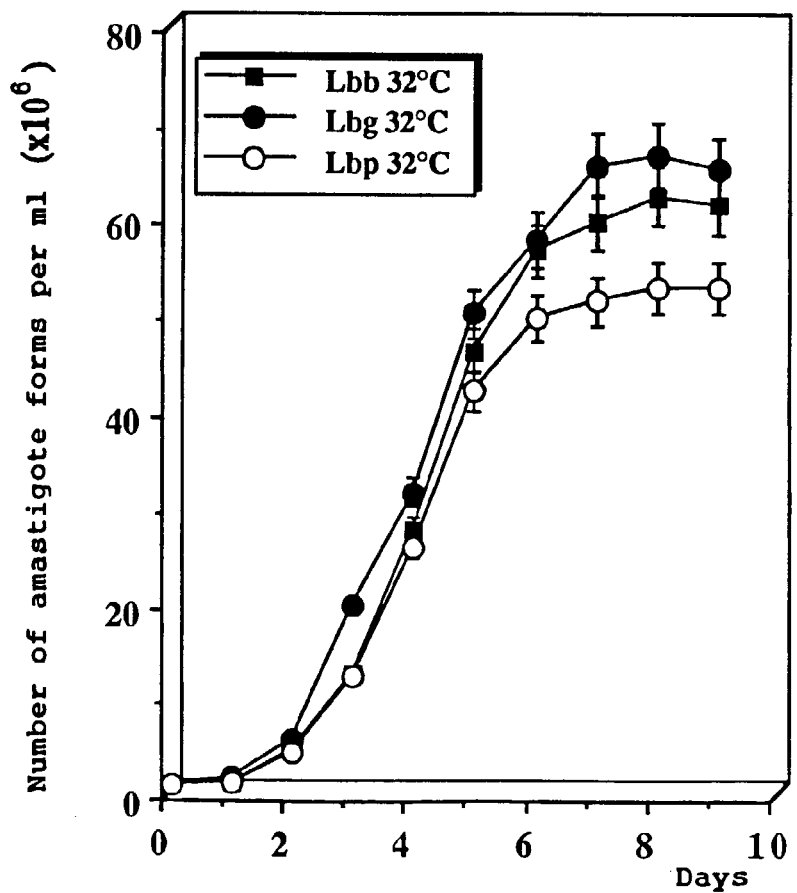
Figure 3B:
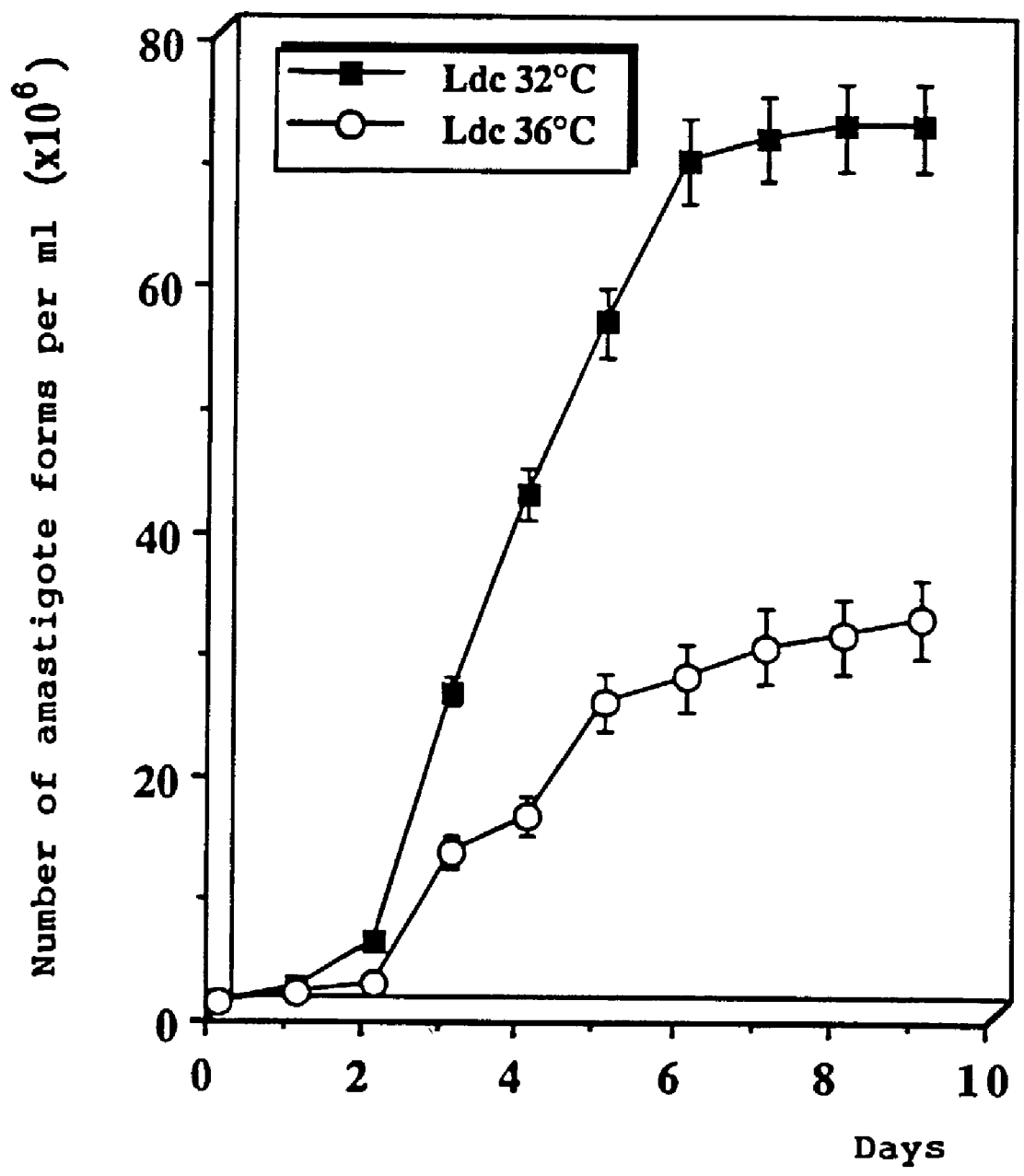
Figure 4A:
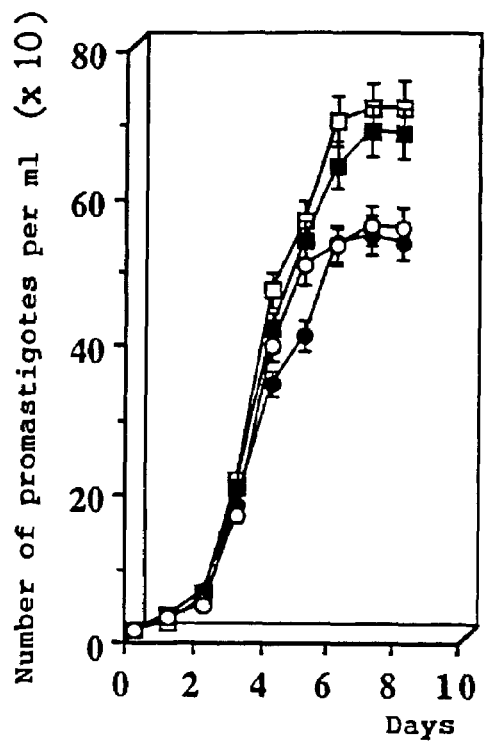
Figure 4B:
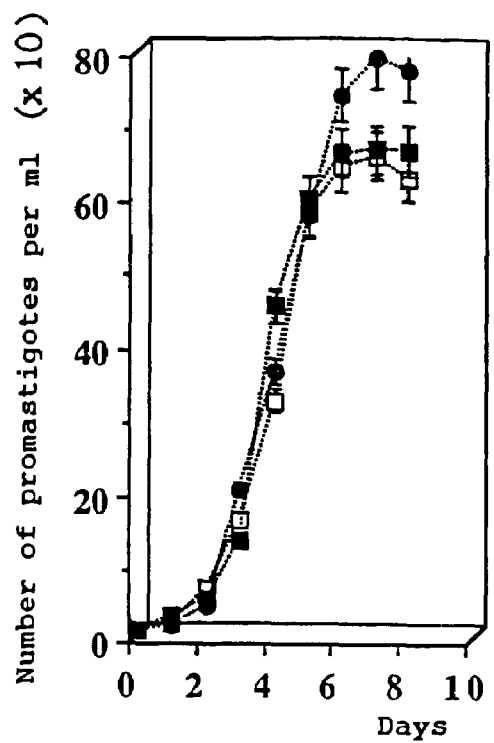
Figure 4C:
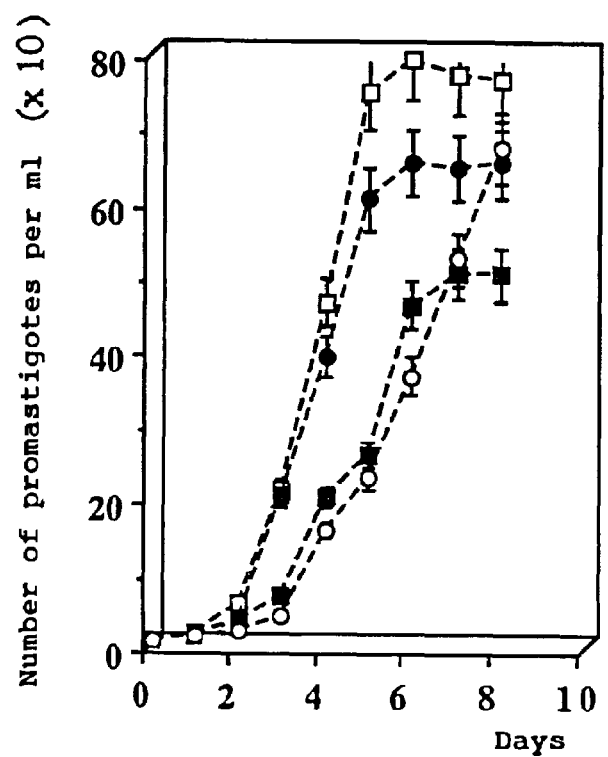
Figure 5A:
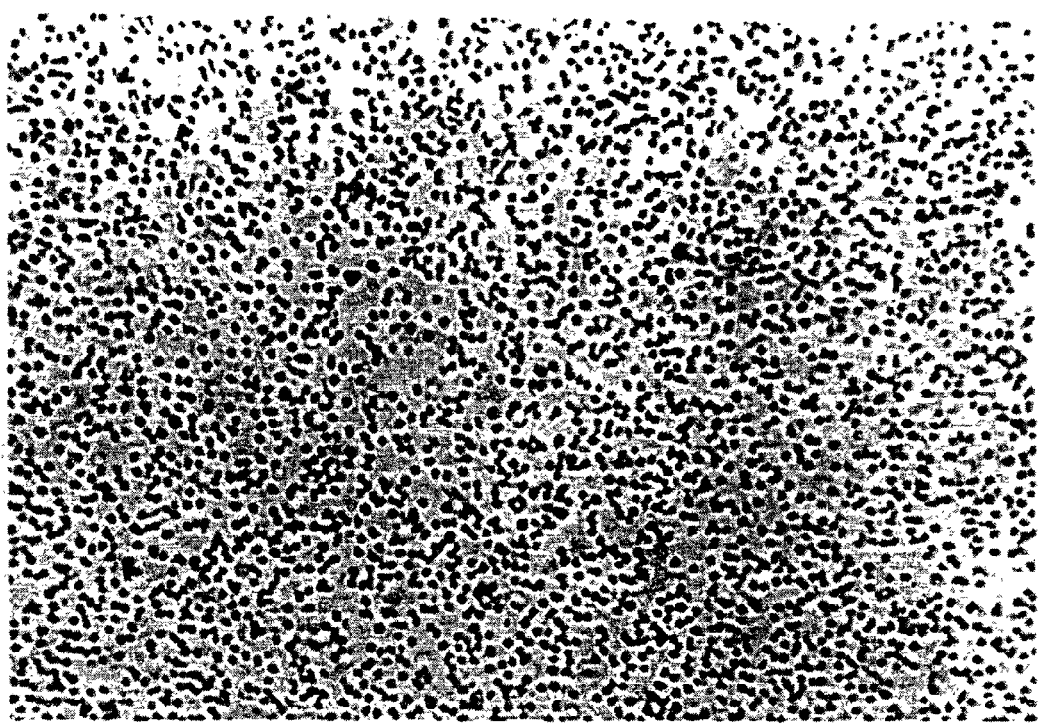
Figure 5B:
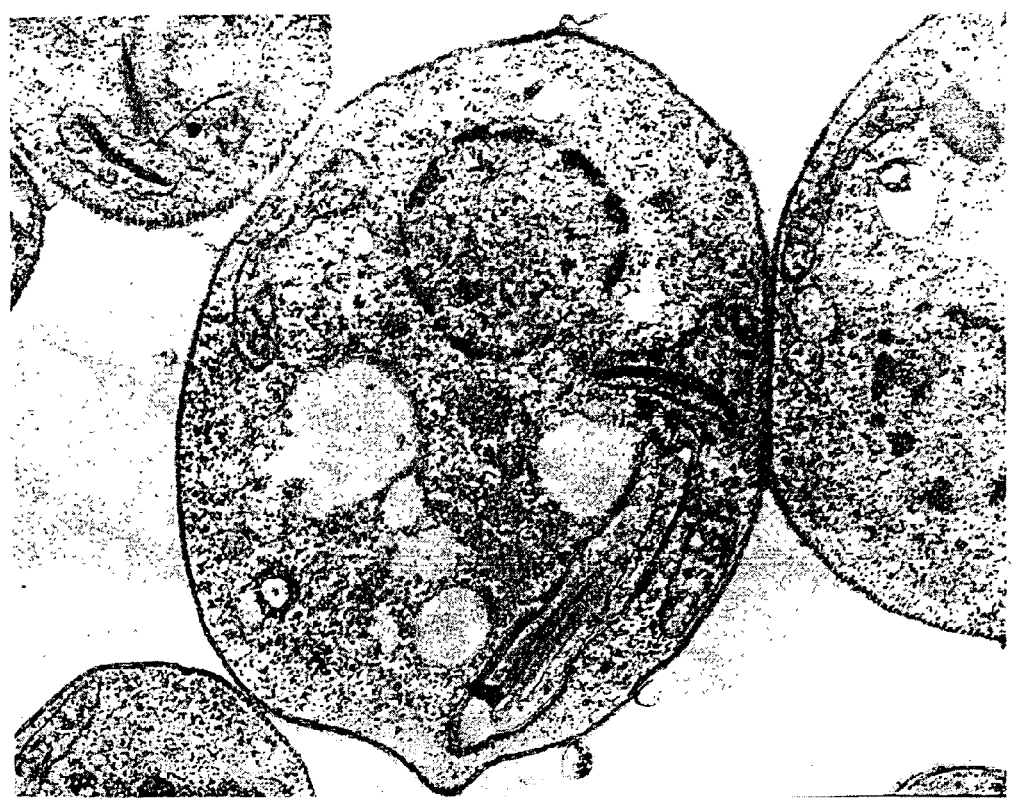
Figure 6A:
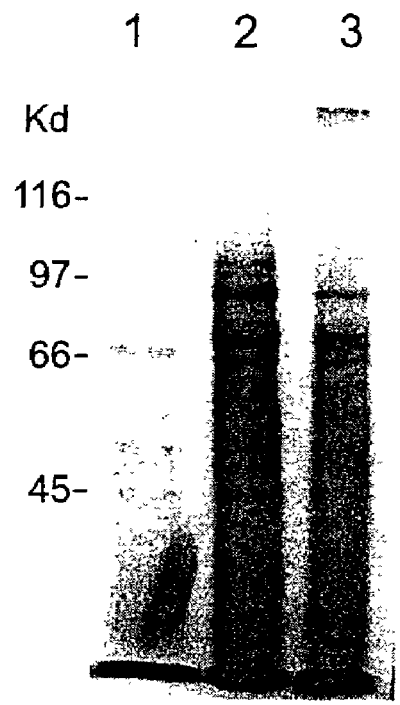
Figure 6B:
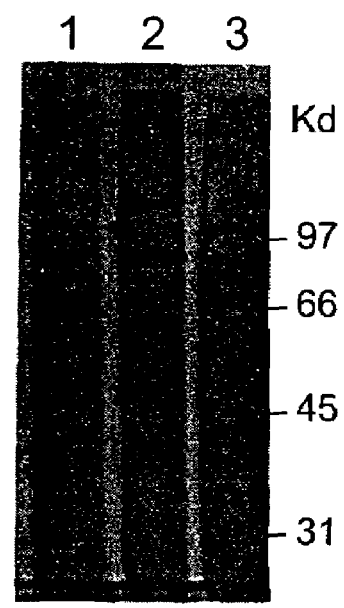
Figure 6C:
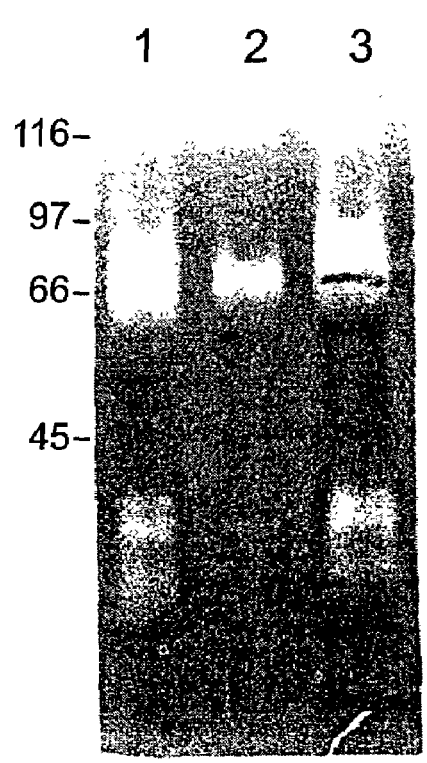
Figure 6D:
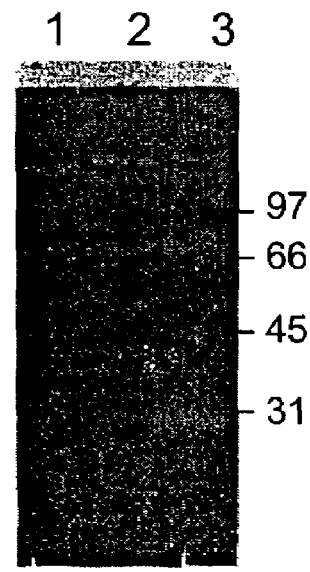
Figure 7A:
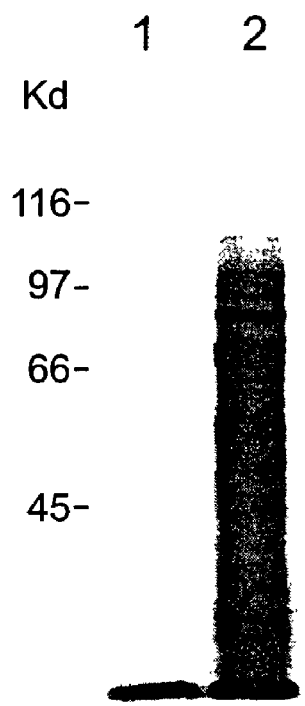
Figure 7B:
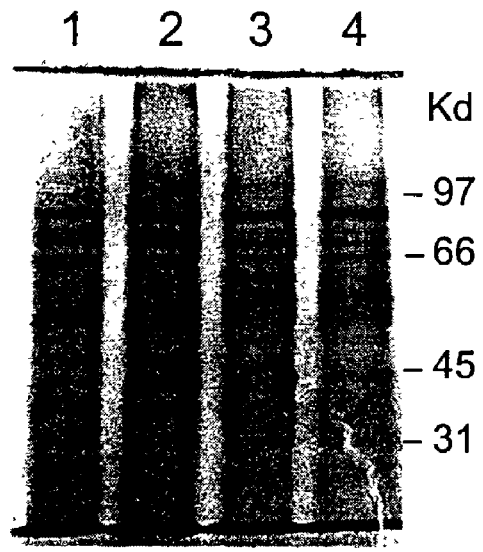
Figure 7C:
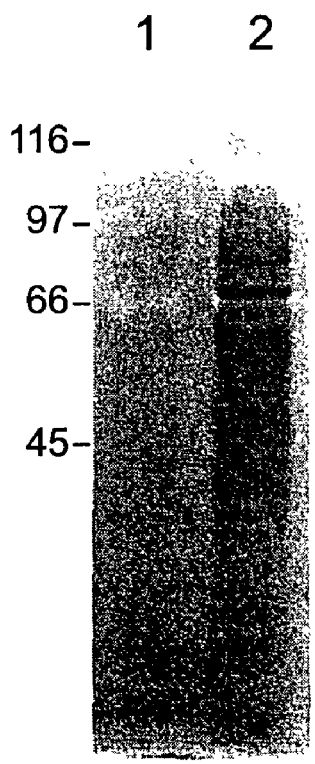
Figure 7D:
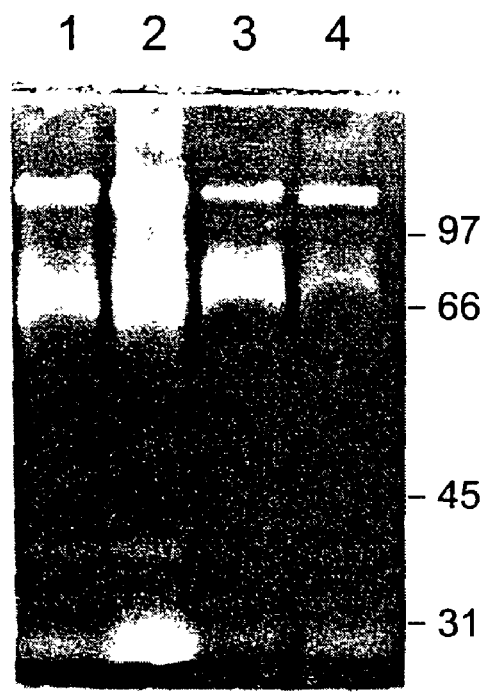
Figure 8A:
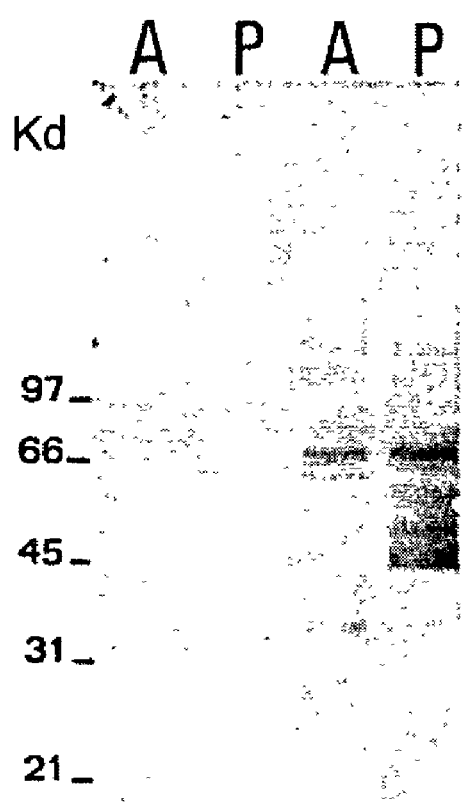
Figure 8B:
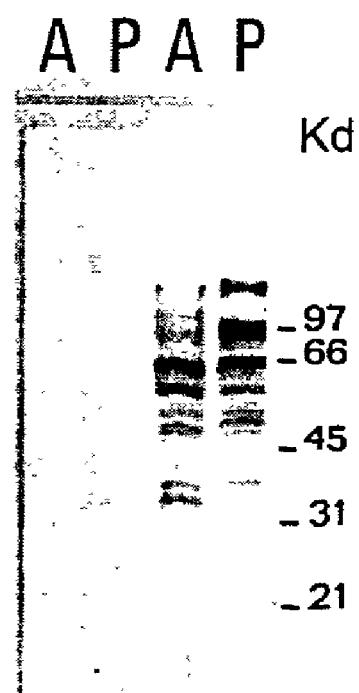
Figure 9:
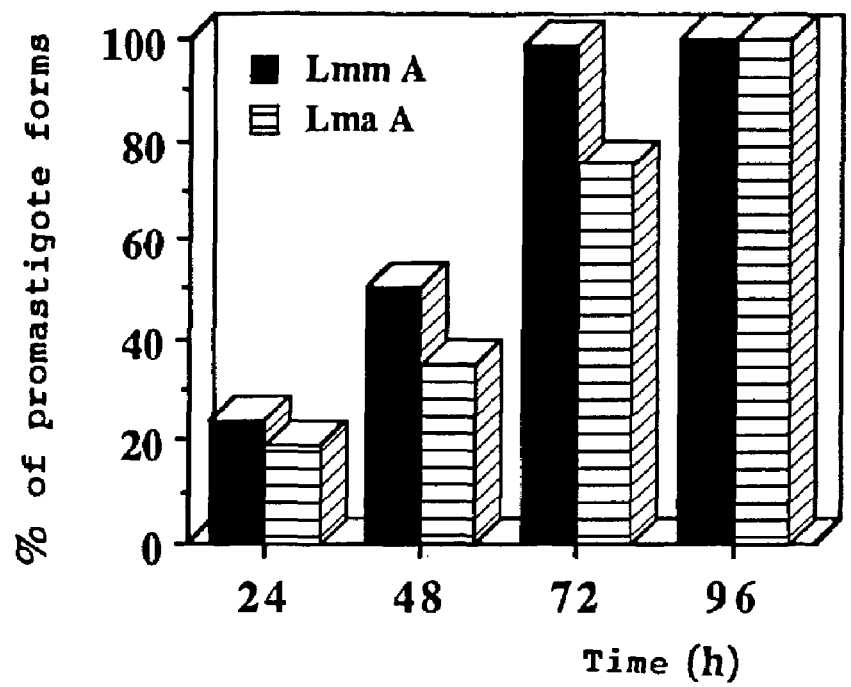
Figure 10:
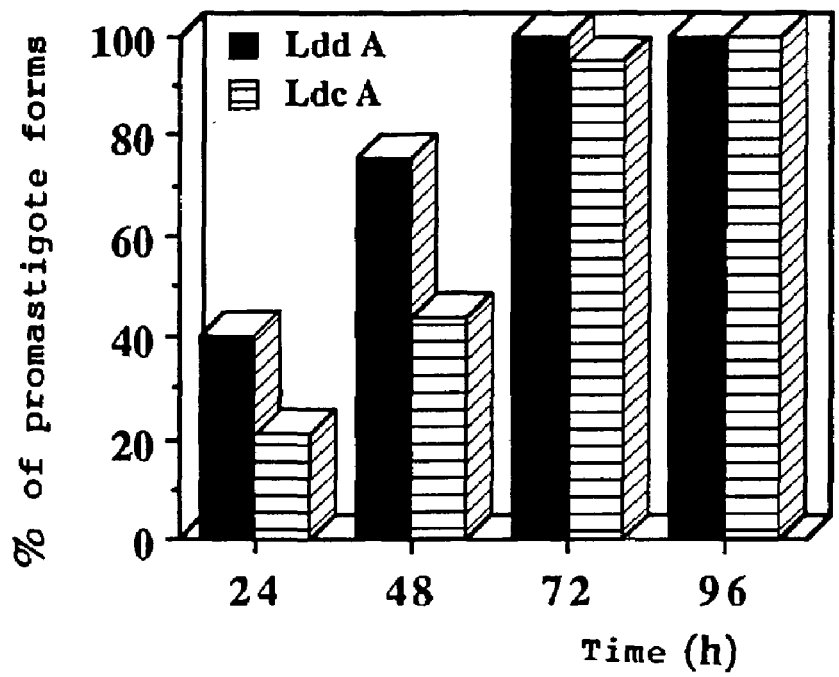
Figure 11:
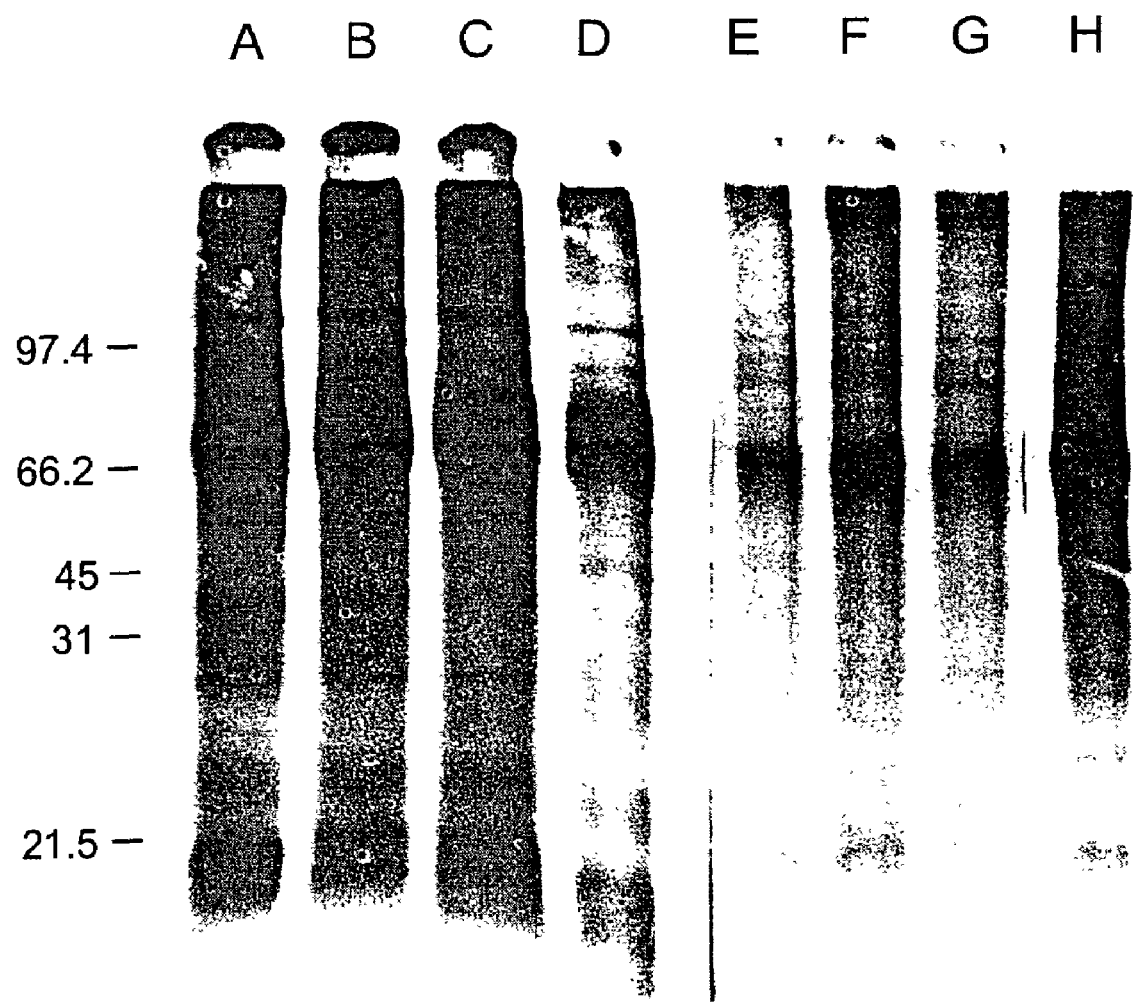
Figure 12:
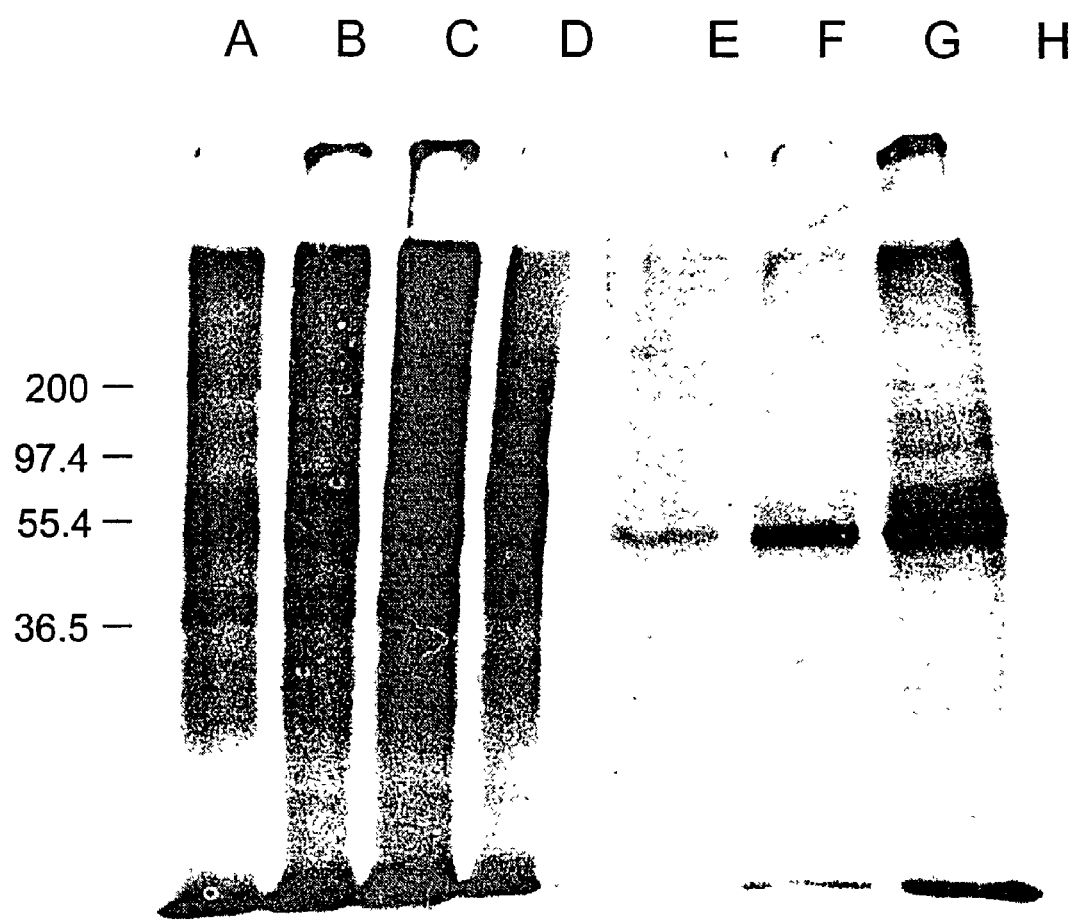
Figure 13:
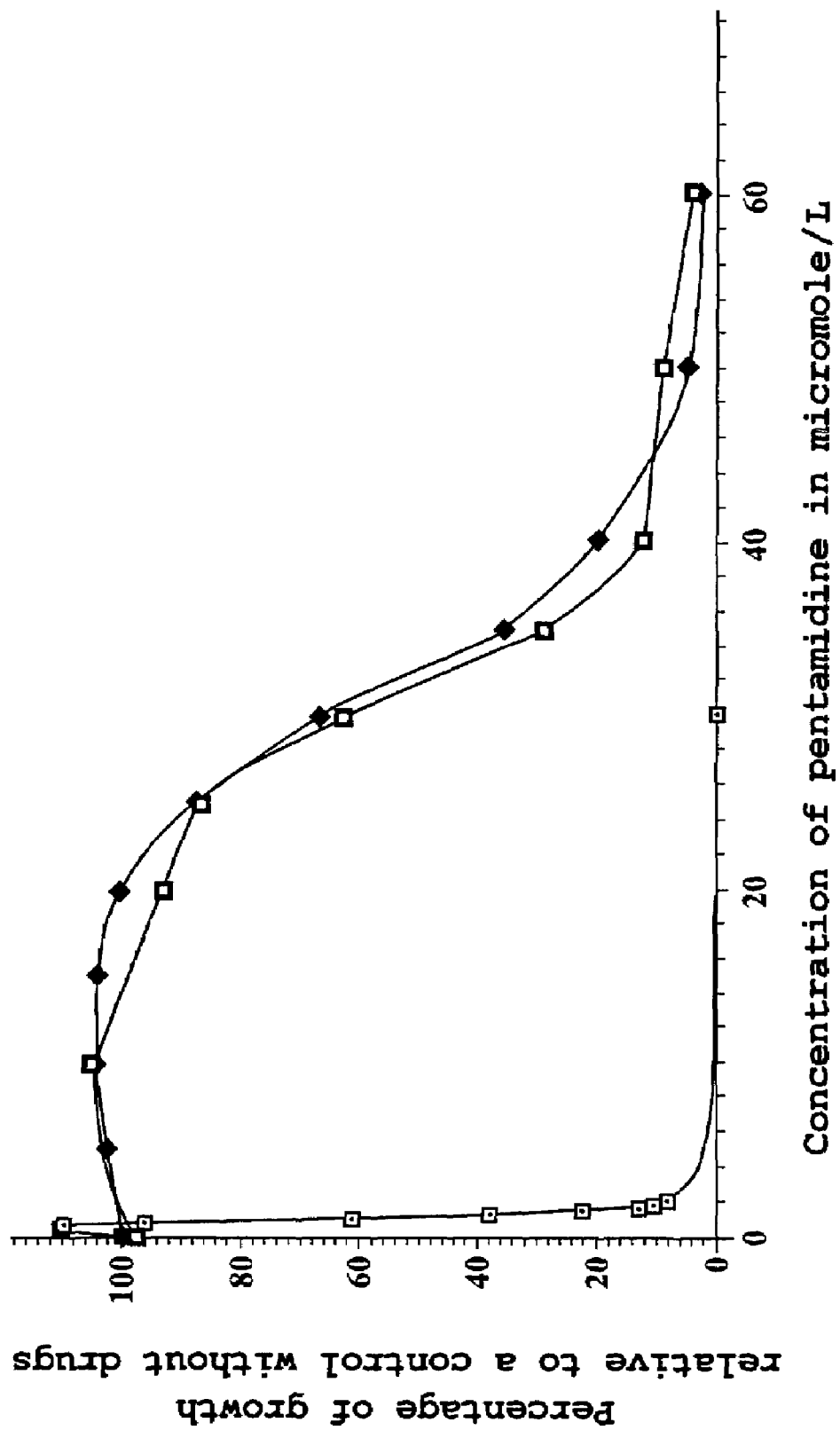

In these examples, reference is made to FIGS. 1 to 13, which represent respectively:

FIGS. 1a and 1b, the differentiation curves of the promastigote forms into amastigote forms and growth of the parasites for *L. amazonensis*, FIG. 2, the percentage of amastigote forms of *L. mexicana* at different culture temperatures, FIGS. 3a and 3b, the culture kinetics of the amastigote forms of various cutaneous and mucocutaneous *Leishmania* (3a) and of a visceral *Leishmania* (3b), FIGS. 4a to 4c, the culture kinetics of promastigote forms of cutaneous and mucocutaneous *Leishmania*, of visceral *Leishmania* and of *T. cruzi*, FIG. 5a, the cytological characteristics and FIG. 5b the ultrastructural characteristics of the amastigote forms of *Leishmania* culture, FIGS. 6a and 6b, the SDS-PAGE electrophoresis analyses using polyacrylamide gel of the total polypeptide profiles of lesion and culture amastigote forms according to the invention, and of promastigote forms of various *Leishmania*, FIGS. 6c and 6d, the electrophoresis analyses using impression gel of the protease activities of these forms, FIGS. 7a to 7d, the analyses indicated above, but relating to visceral *Leishmania*, FIGS. 8a and 8b, the analysis of the antigenic profiles of *Leishmania* by the immunoblotting technique using sera from the homologous immunization of a rabbit, FIGS. 9 and 10, the differentiation kinetics of amastigote forms obtained according to the invention into promastigote forms for cutaneous and mucocutaneous *Leishmania* and for visceral *Leishmania* respectively, FIGS. 11 and 12, the kinetics of incorporation of [$^{35}$S]-methionine by the total proteins or of excretion-secretion of *L. infantum* and *L. amazonensis*, respectively, and FIG. 13, the degree of resistance to pentamidine of parasitic forms of *L. mexicana*.

Examples 1 to 3 relate to culture media which are axenic, or axenic and aseric, but contain macromolecules. These media are described by way of information from the moment they are usable during the adaptation of a parasitic form in a given medium and are then advantageously replaced, during successive passages, by axenic and aseric media, free from molecules non-dialyzable at a cut-off threshold of 3 kDa. According to the application envisaged for the parasitic forms, they can be used in one or more of the stages for producing the development cycle of a parasitic form.

EXAMPLE 1

Production of an Acellular Culture Medium for Amastigote Form of Cutaneous or Mucocutaneous Leishmania or of *T. cruzi*.

The formulation of a culture medium supporting the growth of the amastigote forms under axenic conditions of different species of *Leishmania* responsible for cutaneous and mucocutaneous leishmaniases and of different strains of *T. cruzi* is given in Table 1.

TABLE 1

| Constituents | Quantities per 1 liter |
|---|---|
| Basic medium | |
| 199 H $^R$ medium (×10) (with Hanks' salts)* | 100 ml |
| Soja tryptocasein $^R$ | 5 g |
| NaHCO$_3$ | 0.35 g |
| L-glutamine | 0.75 g |
| HEPES | 5.95 g |
| D(+) glucose | 2.50 g |
| H$_2$O | S.Q. 800 ml |
| additives | |
| Bovine hemin | 0.015 g |
| Foetal calf serum | 200 ml |

*199 H medium marketed by GIBCO BRL, ref 042–01181 in the 1994 catalogue.

This medium, called in the remainder of the examples M1, is prepared as follows:

Soja tryptocaseine $^R$, sodium bicarbonate, L-glutamine, HEPES and D(+) glucose are added successively, in the proportions indicated in the table, to 100 ml of 199H medium (with Hanks' salts). The volume of the medium is then adjusted to 800 ml with deionized-distilled water. This basic medium is kept for several months at −20° C. At the time of its use, bovine hemin (0.023 mM) and foetal calf serum (200 ml) which have been decomplemented beforehand (56° C. for 30 minutes) are added to the 800 ml of basic medium. The resultant medium M1, kept at 4° C., can be used for 3 weeks without alteration to its properties. The pH of the medium is 6.5±0.1 and the osmolarity value was determined at 443.3±2.3 milliosmoles per kg of water.

It should be remembered that the Hanks' salts correspond to the following composition: CaCl$_2$, 2H$_2$O (1.8 g/l), KCl (4 g/l), KH$_2$PO$_4$ (0.6 g/l), MgSO$_4$, 7H$_2$O (2 g/l), NaCl (80 g/l) and NaHPO$_4$, 7H$_2$O, (0.48 g/l). The concentrations indicated correspond to the 199H 10× medium.

EXAMPLE 2

Production of an Acellular Culture Medium for Amastigote Forms of Visceral *leishmania*

L-cysteine (3 mM) and bathocuproine disulphonic acid (0.01 mM) are added to the M1 medium described above. The composition of the medium obtained, called hereafter medium M2, is given in the following Table 2:

TABLE 2

| Constituents | Quantities |
|---|---|
| M1 medium | 1000 ml |
| L-cysteine | 3 mM |
| Bathocuproine disulphonic acid | 0.01 mM |

EXAMPLE 3

Production of Axenic and Aseric Culture Media for Amastigote Forms of *Leishmania*.

Completely defined media supporting the growth of amastigote forms of *Leishmania* under axenic and aseric conditions were perfected. For the amastigote forms, the foetal calf serum of medium M1 or M2 is replaced by a bovine serum albumin (BSA)—linoleic acid complex at a rate of 20 μg of linoleic acid per ml of M1 or M2 medium. The pH of the medium is 6.5±0.1 and the osmolarity value was determined at 467±2.9 milliosmoles per kg of water.

The corresponding composition of the medium obtained, called M3, is given in Table 3 hereafter.

TABLE 3

| Constituents | Quantities |
|---|---|
| M1 or M2 without FCS | 100 ml |
| BSA - linoleic acid | 0.002% (W linoleic acid/V) |

EXAMPLE 4

Production of an Cellular and Aseric Culture Medium, Free From Macromolecules (Composed of Molecules Dialyzable at a Cut-Off Threshold of 3 kda) for Amastigote Forms The formulation of a medium according to the invention for the differentiation and culture of amastigote forms of cutaneous, mucocutaneous and visceral *Leishmania* and of different strains of *T. cruzi* is given in Table 4.

TABLE 4

| Constituents | Quantities for about 800 ml |
|---|---|
| Basic medium | |
| 199H medium $^R$ (×10) (with Hanks' salts) | 100 ml |
| Soja tryptocasein $^R$ | 5 g |
| NaHCO$_3$ | 0.35 g |
| L-glutamine | 0.75 g |
| HEPES | 5.95 g |
| D(+) glucose | 2.50 g |
| H$_2$O | S.Q. 800 ml |
| Modified 199H medium $^R$ (×10)** | 4 ml (5%) |
| additives | |
| Bovine hemin | 0.009 mM |
| Reduced glutathione | 0.08 mM |
| Vitamin solution (×100) | 2% |

*199H medium marketed by GIBCO BRL, ref 042–01181 in the 1992 catalogue
**modified 199H medium marketed by Flow Laboratories, ref 14230–54 in the 1992 catalogue.

The medium, called in the remainder of the examples MA1, is prepared as follows:

First of all the following basic medium is produced:

Soja tryptocasein $^R$, sodium bicarbonate, L-glutamine, HEPES and D(+) glucose are successively added in the proportions indicated in the table to 100 ml of 199H medium (with Hanks' salts), concentrated 10 times (or 10×), as marketed by GIBCO BRL. The volume of the medium is then adjusted to 800 ml with deionized-distilled water. Then modified 199H medium concentrated 10 times, as marketed by Flow Laboratories, is added, which has been heated beforehand at 56° C. for 45 minutes.

This basic medium is kept for several months at −20° C. At the time of its use, bovine hemin (0.009 mM), reduced glutathione (0.08 mM) as marketed by Boehringer Mannheim under the reference 1277*44 and a vitamin solution (2%), concentrated 100 times, such as that marketed by GIBCO BRL, ref 12414-017, are added to the 800 ml of basic medium. The latter solution contains the following vitamins with the concentrations indicated in parentheses: biotin (0.4 mg/L), calcium D pantothenate (0.5 mg/L), choline chloride (6 mg/L), folic acid (2 mg/L), i-inositol (70 mg), nicotinamide (2 mg/L), paraaminobenzoic acid (2 mg/L), pyridoxine-HCl (2 mg), riboflavin (0.4 mg/L), thiamine-HCl (2 mg/L) and vitamin B12 (0.01).

The resultant MA1 medium, kept at 4° C., can be used for 3 weeks without alteration to its properties. The pH of the medium is 6.5±0.1 and the osmolarity value was determined at 412.3±3.1 milliosmoles per kg of water.

EXAMPLE 5

Production of a Culture Medium According to Example 4 Suitable for Amastigote Forms of Visceral *Leishmania*

If necessary L-cysteine (3 mM) and bathocuproine disulphonic acid (0.01 mM) are added to 1000 ml of the MA1 medium of Example 4.

EXAMPLE 6

Production of Axenic and Aseric Culture Media, Free From Macromolecules for the Promastigote Forms The aseric medium devised for the culture of the promastigote forms is constituted by a mixture of commercially-available culture media. 20 ml of modified 199H medium (with Hanks' salts) and 0.5 mg of bovine hemin are added to one liter of RPMI 1640 medium concentrated 1.1 times and containing 5.95 g of Hepes. This medium is kept for 15 days at +4° C. without alteration to its properties. The pH of the medium is 7.2±0.1 and the osmolarity value was determined at 353±3 milliosmoles per kg of water.

The formulation for one liter of culture medium supporting the growth of the promastigote forms of *Leishmania* under aseric conditions is given in Table 5 hereafter and is called MP.

TABLE 5

| Constituents | Quantities |
| --- | --- |
| RPMI 1640 (1.1×) with L-glutamine and HEPES | 1000 ml |

TABLE 5-continued

| Constituents | Quantities |
| --- | --- |
| Modified 199H medium* (10×) | 2% (W/V) |
| Bovine hemin | 0.0005% (W/V) |

*199H medium from GIBCO BRL mentioned above

EXAMPLE 7

Adaptation and Culture of Amastigote Forms of *Leishmania* Under Axenic Condition The promastigote forms of different species of *Leishmania* are cultured, then they are differentiated into amastigote forms.

The results of studies carried out on 19 strains of *Leishmania* are indicated hereafter.

a. *Leishmania* strains.

The principal characteristics (country, hosts, year of isolation and species) are summarized in Table 6 which follows. The subspecific characterization of the different species of *Leishmania* was carried out by genetic typing by analyzing more than 10 variable isoenzymatic loci.

TABLE 6

| Designation of Sources | Species | Number of passages | Number of amastigotes (×10$^7$/ml) |
| --- | --- | --- | --- |
| MHOM/BR/79/LI-01 | L. chapasi | 75 | 7.2 |
| MHOM/MA/67/JTMAP Clone 1 263 | L. infantum | 39 | 7.3 |
| MHOM/MA/27/JTMAP Clone 7 263 | L. infantum | 48 | 6.9 |
| MHOM/IN(—)/61/L-13 | L. donovani | 64 | 5.9 |
| MHOM/—/—/IT-2217 | L. donovani | 56 | 6.1 |
| MHOM/IN/80/Ldd 8 Cl$_2$ | L. donovani | 44 | 5.9 |
| MHOM/IN/80/Ldd 8 Cl$_2$ R60 | L. donovani | 41 | 4.8 |
| MNYC/BZ/62/M-379 | L. mexicana | 167 | 7.5 |
| MHOM/BO/83/LPZ-155 | L. mexicana | 97 | 6.2 |
| MHOM/BR/76/LTB-012 | L. amazonensis | 149 | 7.2 |
| MHOM/BR/73/M-2269 | L. amazonensis | 89 | 5.1 |
| MHOM/BR/75/M-2904 | L. braziliensis | 145 | 6.3 |
| MHOM/BO/90/CS | L. braziliensis | 64 | 6.2 |
| MHOM/BO/90/AN | L. braziliensis | 37 | 5.9 |
| MHOM/BR/75/M-4147 | L. quyanensis | 94 | 6.6 |
| MHOM/BR/78/M-5378 | L. quyanensis | 42 | 5.4 |
| MCHO/PA/00/M-4039 | L. panamensis | 85 | 5.9 |
| MHOM/PA/71/LS-94 | L. panamensis | 74 | 5.2 |
| HOM/EQ/91/A-8044 | L. panamensis | 39 | 4.8 | b. culture of promastigote forms.

The promastigote forms of these different strains of *Leishmania* are cultivated for the purposes of adaptation at 26° C.±1° C. in a liquid monophasic synthetic medium, RPMI 1640, which has added to it 10% foetal calf serum (abbreviated to FCS) which has been decomplemented beforehand at 56° C. for 30 minutes.

The composition of the medium is as follows:

| | |
| --- | --- |
| RPMI 1640 | 10.40 g |
| HEPES | 5.95 g |
| NaHCO$_3$ | 2.20 g |
| H$_2$O | 900.00 ml |

The pH is adjusted to 7.2 with 1N sodium hydroxide; the medium is sterilized by filtration on a Millipore R membrane of 0.22 µl porosity and can thus be kept for one month at 4° C. At the time of its use, 100 ml of decomplemented FCS, is added.

The strains of Leishmania are maintained under routine culture by two weekly subcultures which consist of inoculating 5 ml of medium in a 50 ml culture flask with exponential-phase promastigote forms ($5 \times 10^5$ parasites per ml). The different strains are kept at $-180°$ C. by cryofreezing in the presence of 5% DMSO.

c. In vitro differentiation of the promastigote forms into amastigote forms:

$5 \times 10^7$ promastigote forms, at the end of the exponential phase, of Leishmania, obtained as indicated above, are seeded in 10 ml of M1 culture medium for the promastigotes of cutaneous or mucocutaneous Leishmania and of M2 medium for those of visceral Leishmania.

On different days of the differentiation kinetics, 20.mu.1 of parasitic suspension is deposited on a slide, rapidly dried then fixed with absolute methanol and stained according to the Giemsa method. The percentage of amastigote forms is determined by counting the number of amastigote forms relative to the total number of parasites using photonic microscopy (×400) in 20 successive fields.

These cultures are carried out at a temperature comprised between 28° C. and 36° C.

Operating as indicated above, the tests were duplicated at 28, 32, 34 and 36° C. with L. mexicana and L. amazonensis and 28° C. and 32° C. with L. braziliensis, L. guyanensis and L. panamensis.

The various differentiation curves obtained as a function of the temperature, during a first passage in M1 medium shows that, generally, under the conditions of these experiments,
- the in vitro growth (number of parasites per ml) of. the organisms studied does not really seem to be altered by the increase in the incubation temperature of the culture. Only the multiplication kinetics of L. amazonensis at 36° C. is greatly slowed down;
- the speed of differentiation (% of amastigote forms over time) as well as the percentages of amastigote forms, determined on the eighth day of the culture, increase significantly and in a way which correlates with the rise in the incubation temperature;
- more than 90% of the promastigote forms are transformed into amastigote forms by the end of the various differentiation kinetics and at incubation temperatures higher than or equal to 32° C.

In order to illustrate the results obtained, FIGS. 1a and 1b give the number of parasites per ml (○) and the percentage of amastigote forms (•) as a function of time (in days) for L. mexicana at 34° C. and 36° C. A high differentiation into amastigote forms is observed, which increases with the temperature.

Under the same conditions, but using an M2 medium, the differentiation of visceral Leishmania such as L. chagasi and L. donovani was studied. Similar percentages of amastigote forms are obtained.

It should be noted that for temperatures higher than or equal to 32° C., the transformation of the promastigote forms into amastigote forms is complete in 4 days after a number of passages which varies according to the species of Leishmania studied and which decreases when the incubation temperature is raised. At 32° C., 3 or 4, 6 to 8 and 8 or 9 subcultures are necessary for cutaneous, mucocutaneous and visceral leishmaniases respectively, whilst 2 or 3 and 7 passages at 36° C. are necessary for the cutaneous and visceral leishmaniases studied as represented in FIG. 2 which gives the percentage of amastigote forms as a function of the number of passages for L. mexicana at 34° C. and at 36° C.

d. Growth kinetics of the amastigote forms.

Curves of culture kinetics for the amastigote forms of various species of Leishmania were established at different temperatures. FIGS. 3a and 3b show the results obtained after at least 25 subcultures of $5 \times 10^6$ amastigote forms in 10 ml of M1 medium, at 32° C. for L. braziliensis (•), L. guyanensis (—•—) and L. panamensis (—○—) and at 32° C. and 36° C. for L. chagasi.

The three characteristic phases of the cellular growth cycle usually observed during the culture of the promastigote forms are found:
- a latency phase (2 days),
- an exponential phase during which the parasites multiply rapidly (4 to 5 days according to the species of Leishmania),
- a static phase which corresponds to a stage of nondivision (from the 6th or 7th day).

A multiplication speed is observed, calculated during the exponential phase (corresponding to the actual doubling time) which is approximately the same for the various culture kinetics, but the doubling time of the amastigote forms is significantly different. It varies from 27 to 32 hours according to the species studied (whereas it is only 16 to 21 hours for the corresponding promastigote forms under the same inoculum, medium volume and aeration conditions). Finally, the parasitic concentrations determined at the confluence of the cultures of amastigote forms of Leishmania vary under the conditions of these experiments, from 4.8 to $7.5 \times 10^7$ amastigote forms per ml of culture in 6 or 7 days according to the species studied (see Table 5).

It is possible to cultivate the amastigote forms of the visceral leishmaniases at 34° C. and even 36° C. The growth curves are similar to those obtained at 32° C.

EXAMPLE 8

About $10^7$ amastigote forms at the end of the exponential phase of the principal species of Leishmania, cultivated in M3 medium, are seeded in 5 ml of MA1 medium at various temperatures. Test at 32° C. were carried out in triplicate with L. mexicana and L. amazonensis and L. donovani and at 36° C. for L. infantum.

If the vitamins are omitted from the medium, the amastigote forms are lyzed after the 5th subculture. In the absence of reduced glutathione the cultures persist for 15 passages. The MA1 medium supports the continuous growth (greater than 40 passages) of the amastigote forms under axenic and aseric conditions of the various species of cutaneous and mucocutaneous and visceral leishmaniases.

The culture kinetics curves of the amastigote forms of the various species of Leishmania were established at different temperatures after at least 10 subcultures of $5 \times 10^5$ amastigote forms per ml in 5 ml of MA1 medium. In a general way, they are very similar to those obtained in M3 aseric medium.

Mass cultures, allowing a large production of amastigote forms, were also carried out in 600 ml culture flasks (containing 200 to 300 ml of useful volume) after an intermediate passage in a 200 ml h flask (containing 50 to 75 ml of useful volume). In a general way, about $10^9$ parasites washed three times are obtained per 75 ml of culture.

In a general way, the amastigote forms cultivated under axenic and aseric conditions, and in the absence of macromolecules, keep their infectious power in vitro and in vivo. The polypeptide and protease profiles are similar to those presented by the amastigote forms cultivated under axenic conditions (see the results given for *L. amazonensis* and *L. infantum*).

Table 7 gives the principal characteristics of the strains of *Leishmania* cultivated under axenic and aseric conditions, without macromolecules, in amastigote form.

TABLE 7

| Designation and source | Species | Number of passages | Average Growth ($\times 10^7$/ml) |
|---|---|---|---|
| MHOM/MA(BE)67/IT-263 | L. infantum | 68 | 6.1 |
| MHOM/MA/67/IT-263 clone 2 | L. infantum | 42 | 6.4 |
| MHOM/MA/67/IT-263 clone 7 | L. infantum | 49 | 7.0 |
| MHOM/../../IT-2217 | L. donovani | 49 | 7.3 |
| MHOM/IN/80/DD8 clone 2 | L. donovani | 26 | 6.5 |
| MHYC/BZ/62/M-379 | L. mexicana | 72 | 7.6 |
| MHOM/VE/76/JAP-78 | L. amazonensis | 76 | 6.9 |
| MHOM/BR/76/LTB-012 | L. amazonensis | 42 | 6.9 |
| MHOM/BR/73/M-2269 | L. amazonensis | 85 | 5.9 |
| MHOM/B6/90/CS | L. braziliensis | 16 | 5.8 |

EXAMPLE 9

Adaptation and Continuous Culture of the Promastigote Forms in Completely Defined Media The results of studies carried out on 25 strains of *Leishmania* and one strain of *T. cruzi* are indicated hereafter.

The principal characteristics (country, hosts, year of isolation and species) of these strains are summarized in Table 8 which follows. The subspecific characterization of the various species of *Leishmania* and of *T. cruzi* was carried out by genetic typing by analyzing more than 10 variable isoenzymatic loci.

TABLE 8

| Designation and Source | Species | Number of passages | Number of promastigotes ($\times 10^7$/ml) |
|---|---|---|---|
| MHOM/BR/79/LI-01 | L. chagasi | 249 | 6.6 |
| MHOMLMA(BE)/67/IT-263 | L. infantum | 89 | 5.6 |
| MHOM/MA/67/IT-263 clone 2 | L. infantum | 59 | 6.5 |
| MHOM/MA/67/IT-263 clone 7 | L. infantum | 61 | 7.1 |
| MHOM/IN/83H 570 | L. donovani | 161 | 6.9 |
| MHOM/IN/(—)/61/L-13 | L. donovani | 149 | 7.8 |
| MHOM/../../IT-2217 | L. donovani | 126 | 7.2 |
| MHOM/IN/80/DD8 clone 2 | L. donovani | 129 | 7.3 |
| MHYC/BZ/62/M-379 | L. mexicana | 229 | 7.9 |
| MHOM/B6/83/LPZ-155 | L. mexicana | 102 | 5.6 |
| MHOM/VE/76/JAP-78 | L. amazonensis | 176 | 6.5 |
| MHOM/BR/76/LTB-012 | L. amazonensis | 142 | 6.9 |
| MHOM/BR/73/M-2269 | L. amazonensis | 85 | 7.7 |
| MHOM/BR/72/1670 | L. braziliensis | 111 | 6.5 |
| NHOM/BR/75/M-2904 | L. braziliensis | 99 | 7.1 |
| MHOM/BO/90/CS | L. braziliensis | 86 | 5.8 |
| MHOM/BO/90/AN | L. braziliensis | 59 | 6.1 |
| MCHO/PA/OO/M-4039 | L. panamensis | 107 | 6.6 |
| MHOM/PA/71/LS-94 | L. panamensis | 136 | 5.3 |

TABLE 8-continued

| Designation and Source | Species | Number of passages | Number of promastigotes ($\times 10^7$/ml) |
|---|---|---|---|
| HOM/91/EQ/A8044 | L. panamensis | 98 | 6.8 |
| MHOM/BR/78/M-5378 | L. puyanensis | 76 | 5.3 |
| MHOM/BR/75/M-4147 | L. guyanensis | 113 | 6.2 |
| MHOM/PE/85/FR-6 | L. peruviana | 79 | 5.5 |
| schnur strain | L. maior | 85 | 5.0 |
| LTD | L. tropica | 80 | 6.8 |
| TEHUANTEPEC STRAIN | T. cruzi | 36 | 5.1 | a. Culture of the promastigote forms in completely defined media.

The promastigote forms of the various strains of *Leishmania* are cultivated in a standard condition at 26° C. in RPMI 1640 medium which has added to it 10% foetal calf serum (decomplemented beforehand) as indicated in Example 4b above. The *T. cruzi* strain is cultivated in the same medium, but at an incubation temperature of 28° C.

A progressive adaptation of the promastigote forms cultivated in a standard fashion in RPMI 1640 medium containing 10% foetal calf serum is carried out in M4 medium. All the tests are carried out in duplicate at 26° C.±1° C. for the *Leishmania* and 28° C.±1° C. for *T. cruzi* in a volume of 5 ml of medium in 25 cm² flasks (50 ml). The cultures are first of all diluted to 50% in M4 medium for at least 2 passages which take place every 4 to 5 days, then to ⅕th, to ¹/₁₀th and to ¹/₂₀th for a number of passages which varies, according to the species studied, from 2 to 7 for each new concentration so as finally to carry out subcultures corresponding to an inoculation of $5\times10^5$ parasites per ml of M4 medium.

b. Growth kinetics of the promastigote forms in M4 medium.

The culture kinetics curves of the promastigote forms of species of *Leishmania* and of *T. cruzi* are given in FIGS. 4a to 4c. They were established after at least 30 subcultures of $5\times10^6$ parasites in 10 ml of M4 medium.

FIG. 4a gives the results obtained with *L. braziliensis braziliensis* (—□—) *L. braziliensis guyanensis* (—•—), *L. braziliensis panamensis* (—■—), and *L. peruviana* (—○—), FIG. 4b those with *L. donovani infantum* (—○—) *L. donovani donovani* (—•—) and *L. donovani chagasi* (—■—), FIG. 4c those with *L. mexicana mexicana* (—□—), *L. mexicana amazonensis* (—•—), *L. major* (—■—) and *T. cruzi* (—○—).

The three characteristic phases of the cellular growth cycle observed in a standard fashion during the culture of the promastigote forms are found: a latency phase (2 days), an exponential phase (6 days) and a static phase (from the 7th day).

The actual doubling times, calculated during the exponential phase, are approximately the same for the various culture kinetics. They vary from 23 to 30 hours according to the species of *leishmania* whilst they fluctuate from 16 to 21 hours for the corresponding promastigote forms cultivated in the presence of foetal calf serum under the same inoculum, medium volume and aeration conditions.

Finally, under the conditions of these experiments, the parasitic concentrations determined at the confluence of the aseric cultures (about 7 days) of promastigote forms vary from 5.0 to $7.9\times10^7$ per ml of M4 medium. Certain species of *Leishmania* are routinely maintained by a weekly subculture for more than 3 years.

c. Study of the infectivity in vitro and in vivo of the promastigote forms of aseric culture.

The promastigote forms of aseric culture are harvested at 4° C. by centrifugation at 2500 g. The parasitic pellet is then subjected to three washings, under the same centrifugation conditions, in PBS buffer, pH 7.2. The parasitic concentration is determined using a Thoma counting chamber.

Infectivity in vitro

The results obtained with *L. chagasi, L. donovani, L. amazonensis, L. mexicana* and *L. braziliensis* are reported.

According to the protocol described in Example 7, the peritoneal macrophages of BALB/c mice are infected with stationary-phase promastigote forms at a rate of 10 parasites per macrophage.

Analysis of the kinetics of infectivity in vitro reveals that after 4 hours of incubation, 24% to 70% of the macrophages according to the species studied have promastigote forms attached to their surface. During the kinetics, the percentages of infected macrophages increase to reach 96 to 100% after 48 hours according to the species of *Leishmania*.

These results demonstrate that the promastigote forms obtained according to the invention are capable of infecting macrophages in vitro.

Infectivity in vivo

The results obtained with *L. mexicana* and *L. amazonensis* are given.

Groups of 12 BALB/c mice are respectively infected by sub-cutaneous route in the pad of the rear right paw (the left paw serving as control) with $5 \times 10^7$ promastigote forms (of static phase) according to the invention of *L. mexicana* and of *L. amazonensis*. The size of the lesion which develops at the inoculation point is determined over time.

Characteristic lesions appear from the fifth week of infection. Their size reaches about 5 and 6 mm in the fourth week for *L. mexicana* and *L. amazonensis* respectively.

EXAMPLE 10

Comparison of the Extracellular Amastigote Forms According to Example 7 with Intracellular Amastigote Forms The results obtained with *L. amazonensis, L. mexicana, L. braziliensis, L. chagasi* and *L. donovani* are reported in this example.

obtaining the extracellular forms

The amastigote forms of axenic culture of the various species of *Leishmania* are harvested by centrifugation at 2500 g. The parasitic pellet is then subjected to three successive washings by centrifugation (same conditions) in PBS buffer, pH 7.2. For certain studies and in particular the tests for agglutination by a lectin, a mechanical dissociation is necessary so as to separate the naturally agglutinated parasites. The parasitic concentration is determined using a Thoma counting chamber.

obtaining the intracellular forms

The intracellular amastigote forms of *L. amazonensis* and of *L. mexicana* are isolated from lesions developed at the inoculation point in BALB/c mice having undergone a sub-cutaneous injection, in the pad of the rear right paw, of $5 \times 10^7$ stationary-phase promastigote forms. The lesions are removed and ground up under sterile conditions in a PBS buffer, pH 7.2 containing 2% glucose. A first centrifugation at a slow speed (400 g) allows the ground-up tissues to be removed. The parasitic suspension is then washed three times with PBS by centrifugation at 2500 g. The intracellular amastigote forms are counted in a Thoma chamber.

The intracellular amastigotes of *L. chagasi* and *L. donovani* are obtained from the ground-up spleens of hamsters infected with $5 \times 10^7$ corresponding promastigote forms, inoculated by intraperitoneal route. These forms are isolated as described above.

Morphological study

The cytological characteristics of the cultured amastigote forms according to the invention were compared with the intracellular amastigote forms by light-optical microscopy after fixation and staining of the parasites with Giemsa stain. By way of illustration, the results observed with *L. amazonensis* are given in FIG. 5a. On examination of this figure it is verified that the cultured amastigotes have general morphological characteristics of *Leishmania*: well individualized nucleus and kinetoplast, but also criteria specific to the amastigote forms: round or oval forms of 2 to 5 μm on the largest axis and absence of the flagella. The arrow shown on the figure indicates amastigote forms in the process of division.

An ultrastructural study by scanning transmission electron microscopy allowed confirmation of the ultrastructural analogy between the intracellular and cultured amastigote forms (FIG. 5b).

Study of the infectivity in vitro of the amastigote forms from axenic culture according to the invention.

Peritoneal macrophages from BALB/c mice are recovered by washing the peritoneal cavity. They are distributed into 24-well culture plates in the bottom of which is a 12 mm diameter glass slip, at the rate of $2.5 \times 10^5$ macrophages per well in 500 μl RPMI 10% FCS. The plates are then transferred at 36° C.±1° C. into an atmosphere enriched with 5% $CO_2$, for about 14 hours. Washing is carried out the next day to eliminate the macrophages which have not adhered to the slip. The wells are then infected with the amastigote forms of the exponential phase or stationary phase at a rate of 5 parasites per macrophage.

After 4 hours of incubation at 36° C.±1° C., all the wells are washed three times with RPMI medium which has added to it 10% FCS to eliminate the parasites not attached to the macrophages. Two slips are removed, washed in sterile PBS then dried rapidly, fixed and stained according to the Giemsa method, so as to evaluate the percentage of macrophages infected, and for certain species of *Leishmania*, the number of parasites per macrophage. This operation is repeated after 24, 48 and 72 hours of incubation. The standard deviations are calculated from two values each corresponding to three readings of 500 cells.

Study of the kinetics of infectivity in vitro shows that after incubation for 4 hours, 35% to 75.4% of macrophages according to the species have amastigote forms attached to their surface. After 24 hours, the percentages of infected macrophages (containing amastigote forms) increase and reach 100% after 72 hours for most of the *Leishmania*.

These results demonstrate that the amastigote forms obtained according to the invention are capable of attaching themselves to the macrophages, entering inside them, multiplying inside them and colonizing other macrophages.

Comparative study of the kinetics of infection in vitro with amastigote forms of corresponding intracellular cutaneous *Leishmanias* and visceral *Leishmania* shows that the percentages of macrophages having amastigote forms attached to their surface (4 hours) as well as the percentages of macrophages infected during the time (24, 48 and 72 hours) are very similar.

Study of the infectivity in vivo

The protocols of experimental infection vary according to whether cutaneous leishmaniasis or visceral leishmaniasis is concerned. The results obtained with L. mexicana and L. amazonensis on the one hand and L. chagasi and L. donovani on the other hand are reported.

Cutaneous leishmaniasis $5\times10^6$ intracellular and cultured amastigote forms (of exponential or stationary phase according to the invention) of L. mexicana and L. amazonensis, contained in 25 µl of PBS buffer, are respectively injected into twelve BALB/ mice by sub-cutaneous route through the right hind footpad, the left paw serving as the control. The infection kinetics are monitored by measuring, using a precision vernier caliper, the size of the lesion which has developed at the inoculation point.

Characteristic lesions appear at the inoculation point between the fourth and fifth week of infection. Their size increases rapidly over time and reaches 6 to 7 mm by the ninth week. In the mice infected by L. amazonensis, ulcerous lesions are observed from the seventh week of infection.

A comparative study of the experimental infection curves of the cultured amastigote forms according to the invention and of the intracellular forms shows a very close similarity.

Visceral leishmaniasis

Groups of twelve golden hamsters are respectively infected by an intraperitoneal injection (200 µl) of $5\times10^6$ intracellular and cultured amastigote forms (of exponential and static phase) according to the invention of L. chagasi and L. donovani. Every 21 days, two hamsters per group are sacrificed. The spleen and one kidney lobe are removed and ground up under sterile conditions in 2 ml of PBS buffer. 500 µl of the suspension is cultured in two types of culture medium (5 ml), RPMI medium with the addition of 10% FCS at 26° C. and medium M1 according to Example 1 at 32° C. Subcultures (dilution to one third) are carried out every 4 days. The appearance of promastigote and amastigote forms is monitored over time and the parasitic concentration is evaluated by photonic microscopy.

The culture of the corresponding spleen homogenates on the 21st day of infection shows that, from the second subculture in the above RPMI medium, two to five promastigote forms of L. chagasi per field are observed by light-optical microscopy. With L. donovani, the first promastigote forms are seen to appear after four subcultures. On the 42nd day of the infection, 2 to 5 promastigote forms per field are visualized from the first passage for L. chagasi and during the second subculture for L. donovani. On the 63rd day, more than 10 parasites per field are counted from the first subculture for both species of Leishmania. The culture of the spleen homogenates for both types of visceral leishmaniasis in M1 medium at 32° C. leads to the survival, then the multiplication of the amastigote forms after 4 to 5 subcultures in this medium.

These results demonstrate, unquestionably, that the cultured amastigote forms of the cutaneous and visceral leishmaniases as obtained according to the invention, are infectious in vivo. These results are confirmed by operating under aseric conditions and in the absence of macromolecules.

Modulation of the infectivity in vitro and in vivo of the cultured amastigote forms as a function of the age of the parasites under culture.

Numerous studies provide evidence of a modification of the infectivity in vitro (vis-á-vis the peritoneal macrophages) and/or in vivo (in an experimental model) of the promastigote forms during their maturation under culture. The sequential development from a slightly infectious stage to a very infectious stage has been demonstrated for many species of Leishmania.

Therefore the infectivity in vitro (vis-á-vis the peritoneal macrophages of mice) and in vivo (in an experimental model) of the amastigote forms of axenic culture according to the invention at different phases of their growth was compared.

Study in vitro

The infectivity in vitro of the amastigote forms of the exponential phase and the stationary phase of different Leishmania, as obtained according to Example 4, was compared.

The amastigote forms of the exponential phase are much less infectious than those of the stationary phase. From the 4th hour of incubation, the macrophages which have amastigote forms of the stationary phase attached to their surface are about twice as numerous. The determination of the percentages of macrophages infected during the kinetics of infection reveals differences of the same order in favour of the amastigote forms of the stationary phase.

Study in vivo

Also, comparison of the kinetics of infection in vivo of the cultured amastigote forms of the exponential phase with those of the stationary one shows that the amastigote forms of the stationary phase are more virulent that those of the exponential phase.

Thus it is demonstrated that the increase in infectivity of the cultured amastigote forms of L. amazonensis, L. chagasi, and L. donovani, during their growth, is accompanied by a loss of agglutination by lectin PNA (peanut agglutinin).

EXAMPLE 11

Total Polypeptide Extracts of Cultured Amastigotes According to the Invention and Comparison with Those of the Intracellular Amastigotes Protein assay Pellets of $10^9$ amastigote forms cultured according to the invention and intracellular amastigote forms (static phase), previously washed, are respectively suspended in 500 µl of extraction solution (0.1% NaCl (W/V), 0.1% Triton X100 (V/V)) and subjected to a series of cold sonications of 3 10-second pulses at 30-second intervals. The supernatant obtained after a centrifugation at 14000 g constitutes the total polypeptide extract.

This extract is subjected to a protein assay according to the Bradford method (BioRad Protein Assay Kit II).

Electrophoretic analysis

SDS-PAGE electrophoretic analysis using polyacrylamide gel (non-reducing conditions) was carried out according to the protocol described by Laemmli U. K. et al., 1970, Nature, 227, 680. The proteins are concentrated in a 5% acrylamide gel, then separated on a 10% electrophoresis gel. 50 µg of proteins are deposited per well. Proteins of known molecular weight (Kit Low Weight, Biorad) serve as markers. Migration is carried out under 85 volts for 2 hours at 4° C. in a Tris/glycine buffer, pH 8.3 containing 0.1% (W/V) of SDS.

Staining with Coomassie blue allows the polypeptide profiles to be visualized. The free or complex polysaccharides are revealed using Schiff's reagent.

Photographs of the gels obtained are represented in FIGS. 6a and 6b.

In FIG. 6a, profiles 1, 2 and 3 are the total polypeptide profiles of the promastigote forms, of the cultured amastigote forms and of the lesion amastigote forms respectively of L. mexicana.

In FIG. 6b, profiles 1, 2 and 3 are those of the cultured amastigote forms, of the promastigote forms and of the lesion amastigote forms respectively of L. amazonensis.

A close similarity is observed between the total polypeptide profiles of the axenically-cultured amastigote forms and those of the corresponding lesion amastigote forms (profile 3).

EXAMPLE 12

Analysis of the Protease Activities Using Gelatin-SDS PAGE 5 mg of gelatin is added to the above 10% acrylamide solution. Two types of disclosure are then carried out: the gel is incubated for one hour at ambient temperature.

in a 0.01 M PBS solution, pH 7.2, containing 2.5% (V/v) Triton X100 $^R$ (to eliminate the SDS) then overnight in the PBS buffer only:

in an acetate buffer, pH 5.5, containing 2.5% (V/V) of Triton X100$^R$, then for about 14 hours in the acetate buffer containing dithiothreitol (DTT) (49 mM).

The protease activities are revealed by staining the gel with Coomassie blue. They then appear in white on a blue background.

FIGS. 6c and 6d represent the photographs of the substrate gels. These figures illustrate protease activities of cultured amastigotes (profile 1), of promastigotes (profile 2) and of lesion amastigotes (profile 3), obtained from the L. mexicana and L. amazonensis strains of Example 7 respectively.

As for the corresponding total polypeptide profiles, a close similarity is observed between the profiles of peptidase activities of the cultured amastigote forms and of the intra cellular forms for both species of Leishmania.

EXAMPLE 13

Comparison Between Promastigote Forms and Amastigote Forms of Axenic Culture According to the Invention Protein concentration The determination of the protein concentrations is carried out by spectrophotometry at 595 nm according to the Bradford method starting with a soluble total polypeptide extract corresponding to the extraction from a parasitic pellet of $10^9$ parasites.

Whatever the species of leishmania studied are, the promastigote forms contain about twice as much protein as the. corresponding amastigote forms (4.9±0.7 mg compared to 2.1±0.3 mg per ml).

Comparison of the total polypeptide profiles of cutaneous leishmania.

An SDS-PAGE electrophoretic analysis of these extracts using polyacrylamide gel is carried out. The photographs of the electrophoresis gels obtained with L. mexicana and L. amazonensis are given in FIGS. 6a and 6b.

As FIG. 6a shows, comparative analysis of the polypeptide profiles of the promastigote forms (profile 1) and of the amastigote forms of L. mexicana (profiles 2 and 3) reveals significant quantitative and qualitative differences.

The following will be revealed:

a predominant protein with an apparent molecular weight of about 65 kilodaltons (abbreviated to Kd) specifically revealed by the promastigote forms;

three major polypeptides, having molecular weights comprised between 55 and 90 Kd, revealed by the amastigote forms, but which do not appear to be present in the total polypeptide extract of the promastigote forms.

Some differences are also revealed with L. amazonensis:

a band corresponding to a molecular weight of about 58 Kd, several polypeptides situated in areas of molecular weight comprised between 30 and 55 Kd, as well as bands having molecular weights of greater than 90 Kd, which appear to be specific to the amastigote forms (FIG. 6b).

Analysis of the same parasitic extracts in a polyacrylamide gel stained with Schiff's reagent demonstrates that the culture, according to the invention, of the amastigote forms is accompanied by the increasing expression of a glycosylated molecule with a molecular weight of about 130 Kd.

This molecule appears to be seldom or not at all represented in the corresponding profiles of promastigote forms.

These promastigote forms reveal on the other hand the presence of a glycosylated molecule having a molecular weight of about 50 Kd.

Visceral Leishmania

The total polypeptide extracts of L. donovani and L. chagasi are subjected to an SDS-PAGE electrophoretic analysis using polyacrylamide gel.

The photographs of the total polypeptide profiles respectively obtained are given in FIGS. 8a and 8b.

In FIG. 7a, profiles 1 and 2 correspond to the promastigote forms and to the cultured amastigote forms respectively of L. donovani and in FIG. 7b, profiles 1 and 2 correspond to the promastigote forms and profiles 3 and 4 to the cultured amastigote forms of L. chagasi.

With L. donovani (FIG. 7a) a major protein is observed revealed in the amastigote forms (profile 2) corresponding to a molecular weight of about 85 Kd and a band of about 105 Kd, which are not found with the promastigote forms (profile 1), which reveal as for L. mexicana a specific major band of about 65 Kd.

The amastigote forms of the exponential phase (profile 4) and of the stationary phase (profile 3) of L. chagasi (FIG. 7b) have two major polypeptides corresponding to molecular weights of about 55 and 60 Kd, which are absent from the total polypeptide profiles of the corresponding promastigote forms of the exponential phase (profile 1) and of the static phase (profile 2).

Comparison of the protease activities

Comparative study of the protease activities of the corresponding amastigote and promastigote forms generally reveals profiles of activity which are qualitatively more complex and quantitatively greater for the amastigote forms of Leishmania, allowing the appearance of protease activities specific to the amastigote stage.

of Cutaneous Leishmania

As FIG. 6c shows, the promastigote forms (profile 2) of L. mexicana express a major activity with an apparent molecular weight of about 65 Kd, corresponding to the surface metalloprotease, whilst the amastigote forms (profiles 1 and 3) present:

a complex of bands which encompasses this molecular weight (from 60 to 85 Kd), activities with a higher molecular weight (greater than 110 Kd) with migration distances varying according to the parasitic stage, three protease activities having molecular weights comprised between 17 and 35 Kd revealed specifically by the amastigote forms.

A minor band with a molecular weight of about 25 Kd, which must correspond to a cysteine protease activity, only revealed for the promastigote forms.

Such differences are also revealed for *L. amazonensis* (FIG. 6*d*). The major protease activities of the promastigote forms (profile 2), with molecular weights of about 65 Kd and 115 Kd, present, for the amastigote forms (profiles 1 and 3), significantly quicker electrophoretic migrations. At least three protease activities having molecular weights comprised between 24 and 36 Kd are revealed specifically by the amastigote forms; only one minor band with a molecular weight of about 24 Kd and which must correspond to a cysteine protease activity is revealed for the promastigote forms of the stationary/phase.

of Visceral *Leishmania*

For *L. donovani* (FIG. 7*c*), the major protease activity of the cultured amastigote forms (profile 2) corresponding to a molecular weight of about 105 Kd is not expressed for the promastigote forms (profile 1). The aforementioned forms reveal a minor band of about 65 Kd, which is also weakly found for the amastigote forms.

For *L. chagasi* (FIG. 7*d*), two protease activities, with molecular weights of -about 28 and 110 Kd, are present both for the amastigote forms of the exponential phase (profile 1) and static phase (profile 2) and for the corresponding promastigote forms (profiles 3 and 4). These two activities are however more intense for the amastigote forms of the static phase. The amastigote forms of the exponential and static phase present metalloprotease activities which are more complex than those expressed by the corresponding promastigote forms. Finally, two activities having molecular weights of about 35 and 48 Kd are specific to the amastigote forms.

Antigenic analysis

Comparative study of the antigenic profiles of the promastigote and amastigote forms was carried out by the immunoblotting technique using rabbit sera immunized with total polypeptide extracts of cultured amastigote forms according to the invention.

The total polypeptide extracts of the promastigote and amastigote forms are separated on SDS-PAGE polyacrylamide gel, transferred onto a nitrocellulose membrane which is incubated in the presence of the corresponding immunization sera. The antigen/antibody complexes are revealed by an antibody conjugated with the peroxidase directed against the initial antibodies.

FIG. 8*a* illustrates the results obtained by putting axenically-cultured amastigote forms and promastigote forms of *L. amazonensis* in contact with a rabbit immunoserum directed against the amastigote forms of *L. amazonensis*. It is observed that four antigens are specifically recognized for the amastigote forms:

a major antigen with an apparent molecular weight of about 62 Kd whose migration is slower for the promastigote forms (65 Kd), three other molecules corresponding to respective molecular weights of about 81, 58 and 35 kd which are not revealed for the promastigote forms, two antigens of promastigote forms having molecular weights of about 45 and 50 Kd, which are more readily recognized by this same immunoserum.

FIG. 8*b* corresponds to the amastigotes and promastigotes of *L. mexicana* vis-á-vis the rabbit immunoserum directed against the amastigote forms of *L. mexicana*. Examination of this figure shows that four antigens corresponding to molecular weights of about 98, 90, 53 and 35 Kd are revealed only for the amastigote forms.

Comparison of the Humoral Response vis-á-vis Axenically-cultured Amastigote Forms of the Invention and Corresponding Promastigote Forms.

The intensity of the response in antibodies is evaluated by the indirect immunofluorescence technique (IIF). The latter consists of semi-quantitatively detecting the circulating antibodies and has the specific feature of using whole parasites fixed to 0.1% gutaraldehyde as antigenic substrate.

Study with immunization sera

Anti-*L. mexicana* and anti-*L. amazonensis* rabbit immunosera are tested in dilution on the promastigote and amastigote forms of the static phase of *L. mexicana* and *L. amazonensis*.

Rabbit sera, removed before immunization, were used to determine the positivity thresholds of the tests. They are 1/2 for *L. amazonensis* and 1/10 for *L. mexicana*.

The results are given in Table 9 which follows in which the anti-*L. mexicana* rabbit antiserum is called anti-Lma IS and the anti-*L. amazonensis* rabbit antiserum is called anti-Lma IS. The letters A and P represent the amastigote and promastigote forms respectively.

TABLE 9

| SERA/PLATES | Lma P | Lma A | Lmm P | Lmm A |
|---|---|---|---|---|
| anti-Lma A IS | — | +1/5 | — | +1/40 |
| anti-Lmm A IS | — | +1/80 | — | +1/40 |

Examination of this table shows that the two rabbit immunosera have only positive reactions with the cultured amastigote forms of the two species of *Leishmania*. Fluorescence is observed on the surface of the amastigote forms in the form of a bordline and at the level of the flagellar pocket. These results clearly demonstrate that the amastigote forms of *Leishmania* express, on their surface and at the level of the flagellar pocket, antigens specific to stages common to both species studied.

Study with experimental infection sera

Hamster sera, infected by promastigote forms of *L. mexicana* and *L. amazonensis* respectively, are removed at different times of the experimental infection which are 30 (D30), 50 (D50) and 221 (D221) days for *L. amazonensis* and 30 (D30), 90 (D90) and 180 (D180) days for *L. mexicana*. These different sera are tested in dilution on the promastigote and amastigote forms of the static phase of *L. mexicana* and *L. amazonensis*. The positivity thresholds are determined using healthy hamster sera. It is 1/20 whatever the species and the parasitic stage analyzed.

The results obtained are summarized in Table 10 which follows, according to which anti-Lma EIS and anti-Lmm EIS represent the anti-*L. mexicana* and anti-*L. amazonensis* experimental infection sera respectively.

TABLE 10

| SERA/PLATES | Lma P | Lma A | Lmm P | Lmm A |
|---|---|---|---|---|
| anti-Lma EIS D30 | — | 1/40 | — | — |
| anti-Lma EIS D50 | 1/20 | 1/160 | — | — |
| anti-Lma EIS D221 | 1/20 | 1/160 | — | 1/20 |
| anti-Lmm EIS D30 | — | — | — | 1/40 |
| anti-Lmm EIS D90 | — | 1/20 | 1/40 | 1/80 |
| anti-Lmm EIS D180 | — | 1/40 | 1/40 | 1/160 |

The early infection sera (D30) react specifically and only with the amastigote forms of the same species. In a general way, the antibody titers obtained vis-á-vis the amastigote forms increase during the two infection kinetics. The D50 and D221 sera of *L. amazonensis* and D90 and D180 sera of

*L. mexicana* also reveal slightly positive reactions (1/20th and 1/40th respectively) with the corresponding promastigote forms. The antibody titers obtained are always less than those revealed with the amastigote forms. Finally the D221 serum of *L. amazonensis* and D90, D180 sera of *L. mexicana* weakly and solely recognize the amastigote forms of the heterologous species.

These results confirm the existence of antigens specific for the amastigote stage. They also demonstrate that the humoral response generated during the experimental infections is more specifically directed against epitopes expressed by the amastigote forms. Finally, they show that the antigens of amastigote forms are more capable of detecting an early infection.

Study of the humoral response during canine leishmaniasis

The study of the humoral response is carried out by indirect immunofluorescence on 39 sera of dogs infected with leishmania. It consists of comparing the antibody response vis-á-vis two antigenic substrates, namely the promastigote, and amastigote forms of the static phase of *L. chagasi*. Two groups of sera are used: 20 sera having antibody titers less than or equal to 1/160th ("slightly positive") and probably corresponding to early infections and 19 sera revealing titers greater than or equal to 1/1280th (highly positive), indicating well-established infections.

The positivity threshold is determined using 12 sera of dogs free from leishmaniasis. Under the experimental conditions used with dilutions of fluorescent conjugate and Evans blue, whatever the indicated antigen used, the positivity threshold is established at 1/40th.

The results of this study are represented in Tables 11A and 11B which follow in which Ldc=*L. chagasi*, Table 11A corresponding to the so-called slightly positive sera and Table 11B to the so-called highly positive sera.

TABLE 11A

| Compared indicated antigens | Number of sera | Differences expressed in antibody titers obtained for the two antigenic substrates | | |
|---|---|---|---|---|
| | | Mean deviation | Minimum deviation | Maximum deviation |
| Ldc A > Ldc P | 12 | 2.0 ± 1.2 | 1 | 4 |
| Ldc A = Ldc P | 3 | 0 | 0 | 0 |
| Ldc A < Ldc P | 5 | 2.2 ± 1.3 | 1 | 4 |

Of the 20 "slightly positive" sera, 12 of them have higher antibody titers, 3 have equivalent titers and 5 have lower titers vis-á-vis the promastigote forms of *L. chagasi* (Table 11A). The deviations expressed in higher or lower numbers of antibody titers are very great and vary from 1 to 4 titers.

TABLE 11B

| Compared indicated antigens | Number of sera | Differences expressed in antibody titers obtained for the two antigenic substrates | | |
|---|---|---|---|---|
| | | Mean deviation | Minimum deviation | Maximum deviation |
| Ldc A > Ldc P | 17 | 2.5 ± 1.6 | 1 | 6 |
| Ldc A = Ldc P | 2 | 0 | 0 | 0 |
| Ldc A < Ldc P | 0 | / | / | / |

As Table 11B shows, the comparative analysis of the "highly positive" sera is even more convincing. In fact, all the sera reveal more intense reactions with the amastigote forms of *L. chagasi*, with higher deviations in the number of antibody titers ranging from 1 to 6.

This new experimental model makes it possible to reveal an improved sensitivity of the indirect immunofluorescence technique using as antigenic substrate the axenically-cultured amastigote forms compared with the corresponding promastigote forms.

EXAMPLE 14

Adaptation of the Cultured Amastigote Forms in Completely Defined Media

The amastigote forms of various *leishmania* were adapted in M3 medium according to Example 3, amongst which were those of *L. mexicana, L. amazonensis, L. braziliensis* and *L. chagasi*.

A progressive adaptation in the medium is carried out as follows: about $10^7$ cultured amastigote forms according to Example 4 are inoculated in 5 ml of medium containing 25% then 50% then 75% and finally 100% of M4 medium.

At each concentration, 4 to 5 subcultures are carried out at a rate of one, then two passages per week.

The culture kinetics of the amastigote forms of axenic and aseric culture of the different species of *leishmania* studied, after more than 20 subcultures in M3 medium, are similar to those determined in the M1 medium.

EXAMPLE 15

Production of the Parasitic Cycle In Vitro a. Under axenic conditions:

$10^7$ amastigote forms of the exponential phase obtained according to Example 4 are seeded in 10 ml of RPMI medium with 10% FCS added to it at 26° C. On the different days of the culture, 20 µl of the parasitic suspension is deposited on a plate, dried rapidly then fixed with absolute methanol for 2 minutes, stained according to the Giemsa method for 10 minutes. The percentage of promastigote forms is determined by counting using light-optical microscopy (×400) over 20 successive fields. Successive subcultures are carried out every 4 days at a rate of $10^6$ parasites per ml before establishing the differentiation kinetics curves. The percentage of promastigotes obtained is represented in FIGS. 9 and 10 as a function of the time (in hours) with *L. braziliensis* (filled), *L. guyanensis* (stripped), *L. panamensis* (stippled) (FIG. 9) and *L. chagasi* (filled) and *L. donovani* (stripped) (FIG. 10).

Examination of these figures shows that the transformation of the cultured amastigote forms into promastigote forms at 26° C. is complete in 4 days for all the species of *Leishmania* studied.

These promastigote forms, also called primary culture or short-term promastigotes, seeded in the M1 medium at a rate of $10^6$ parasites per ml, differentiate very rapidly (3 to 4 days) into amastigote forms at 32° C. The transformation is complete after 2 to 5 successive subcultures according to the species of *leishmania* studied.

By this process, it is therefore possible to obtain in vitro the different parasitic stages of the *Leishmania* and this can be done much more quickly and easily than by the in vivo techniques used at present (experimental infections). Furthermore, the parasitic forms thus produced are free from any cellular contaminant and are capable of multiplying in vitro (the amastigote forms isolated from infected tissues survive 2 to 3 days), which makes it possible to have available an abundant source of the two parasitic stages of the principal species of *Leishmania*.

The experimental infection kinetics with BALB/c mice of the short-term promastigote forms of the exponential phase and the long-term and short-term promastigote forms of the stationary phase were studied. The results obtained for *L. amazonensis* showed that it is possible to restore the infectivity of the "long-term" promastigote forms by creating the parasitic cycle in vitro. The same demonstration was carried out for visceral *Leishmania* both in vitro and in vivo.

The infectivity in vivo of the cultured amastigote forms was also studied during the various successive subcultures (17, 59 and 143 subcultures). The infectivity kinetics obtained are not significantly different as a function of the number of passages under culture. These results show that, unlike the corresponding promastigote forms, the "long-term" culture of the cultured amastigote forms does not lead to a loss of their infectivity in vivo.

b. Under axenic and aseric conditions

The results obtained with *L. chagasi* and *L. amazonensis* are reported. $10^7$ aserically-cultured promastigote forms at the end of the exponential phase/beginning of the stationary phase are inoculated in 10 ml of M3 medium according to the invention and incubated at 32° C.±1° C. The percentage of amastigote forms obtained as a function of time is determined according to the protocol described previously. The differentiation of the promastigote forms into amastigote forms is complete in 48 hours for the two species studied. It is then possible to cultivate the amastigote forms under axenic and aseric conditions as indicated in Example 10.

$10^7$ cultured amastigote forms recently transformed from aserically-cultured promastigote forms are seeded at 26° C.±1° C. in 10 ml of M4 medium according to the invention. The transformation of the amastigote forms into promastigote forms is then complete in 3 to 5 days. The promastigote forms thus obtained, also called primary-culture or short-term promastigotes, are maintained under culture in M4 medium by a weekly subculture as indicated in Example 5, a.

The processes for adaptation and culturing, perfected on the principal species of *Leishmania*, were applied to the culture of the amastigote forms of strains of *T. cruzi*, which is the agent for Chagas' disease.

The results obtained with strains SO 34 cl 1, Gamba cl 1 and SO 3 cl 1 are reported hereafter, isoenzymatically typified by the analysis of more than 15 loci. These strains were rapidly adapted and cultivated in M1 medium at 32° C. starting from the corresponding metacyclic trypomastigote forms (infectious forms of the vector insect). The trypomastigote forms are obtained from the epimastigote forms (multiplication forms of the vector insect) cultivated in LIT medium containing 10% FCS, according to a protocol described by Contreras et al. (1985, Mol. Biochem. Parasitol., 16, 315). $5 \times 10^7$ epimastigote forms are incubated for 2 hours in a TAU synchronization medium (8 mM phosphate buffer, 190 mM NaCl, 17 mM KCl, 2 mM $CaCl_2$, pH 6), then in a TAUP differentiation medium (10 mM TAU+L-proline, 2 mM L-aspartic acid, 50 mM L-glutamine and 10 mM D-glucose) until a total transformation of the epimastigote forms into trypomastigote forms is obtained. About $5 \times 10^7$ metacyclic trypomastigote forms are seeded in 10 ml of M1 medium at 32° C. The differentiation into amastigote forms is complete after 4 successive subcultures with strains SO 34 and Gamba and 11 subcultures for strain S 03. Strains of this type are cultivated under axenic condition in a continuous fashion by weekly subculture and have undergone more than 25 passages in M1 medium.

Under light-optical microscopy, the cultured amastigotes of *T. cruzi* present general morphological characteristics of the intracellular amastigote forms. A mass culture (200 ml) of strain SO 34 cl 1 was carried out. About $10^9$ washed parasites (three washings in PBS buffer pH 7.2) are obtained from 50 ml of culture.

Various tests for the differentiation of the cultured amastigote forms of strains SO34 and Gamba into epimastigote forms (multiplication forms of the vector insect) or into sanguicolous trypomastigote forms (infectious forms of the host) were also carried out. When $5 \times 10^6$ cultured amastigote forms are inoculated in 10 ml of M1 medium containing 10% calf serum, then incubated at 26° C. or at ambient temperature for 48 hours, the culture contains more than 90% of epimastigote forms. On the other hand, when a culture of amastigote forms at the end of the exponential phase is incubated at 37° C. in the presence of 5% $CO_2$ in an M1 medium containing 30% and more of foetal calf serum for 4 days, 30 to 40% of the amastigote forms are transformed into trypomastigote forms. It is therefore possible by adjusting the incubation temperature conditions and the concentrations of foetal calf serum to produce in vitro the cycle of *Trypanosoma cruzi* (epimastigote forms, metacyclic trypomastigote forms, amastigote forms and sanguicolous trypomastigote forms) under axenic conditions.

EXAMPLE 16

Study of the Direct Leishmanicidal Effect on the Cultured Amastigote Forms of Nitric Oxide, a Molecule which Brings About Macrophage Activation There have recently been described antimicrobial activities of nitric oxide synthesized by macrophages activated according to a new metabolic route leading to the synthesis by the activated macrophage of derivatives of nitric oxide (NO, $NO_2$— and $NO_3$—) starting with L-arginine. This molecule which brings about non-specific immunity is also responsible for anti-parasitic activities (trypanostatic effect in the case of African trypanosomas and on *Toxoplasma gondii* and lytic effect on *Schistosoma mansoni* and *Leishmania major*.

Thanks to the new experimental model of the invention, a leishmanicidal activity directly directed against the cultured amastigote forms of various species of *leishmania* could be demonstrated. Also, one of the mechanisms leading to lysis of the amastigote forms was elucidated. In fact, the studies carried out demonstrated that the inhibition of cis-aconitase (Krebs cycle enzyme), due to the interaction of NO with the Fe—S prosthetic group (Iron-sulphur) of this enzyme brings about parasitic lysis. These results were obtained by pulsing gaseous NO (1%), carried by nitrogen (99%) free from oxygen, directly over the cultured amastigote forms of *L. mexicana, L. amazonensis, L. braziliensis* and *L. chagasi* for 15 minutes.

The culture kinetics as well as the differentiation of the amastigote forms into promastigote forms were monitored after this treatment. In certain experiments, media containing 100 μm of $FeSO_4$ (iron source) or alpha-ketoglutaric acid (3 mM) and cis-aconitate (3 mM) added immediately to the parasites treated with NO restore the growth of the amastigote forms.

The comparative study of different enzymatic activities, and in particular that of the Krebs cycle, on the amastigote forms treated or not treated with NO made it possible to reveal an inhibition of cis-aconitase by NO.

EXAMPLE 17

Use of Leishmanial Exoantigens in an ELISA Technique for the Detection of Circulating Antibodies in Visceral Leishmaniasis.

a) Protocol
Sensitization of the plates
The supernatants of axenic and aseric cultures of promastigote forms of *L. infantum* (6, 15 and 21 days) are collected by centrifugation and filtered on a 0.22 µm Millipore $^R$ membrane. They are diluted to 50% in a carbonate buffer (0.5 M, pH 9.6) so as to obtain respective concentrations of 3.5, 4.6 and 7.0 µg/ml (protein equivalent).
100 µl of these solutions is deposited in each well of the microtitration plates. Sensitization lasts for 2 hours at 37° C., then overnight at 4° C.
Washings
3 5-minute washings are carried out by repassage through filter paper in a washing buffer (0.01 M PBS, pH 7.2 containing 0.05% Tween 80).
Saturation of the non-specific fixation sites
100 µl of fixing buffer (washing buffer containing 0.25% gelatin) is distributed into each well, then the mixture is incubated for 30 minutes at 37° C.
Washings
3 5-minute washings in a washing buffer are carried out.
Distribution of the sera
Dog or human sera are diluted to ½00th in the fixing buffer. 100 µl of serum is deposited per cell. Incubation is carried out for 30 minutes at 37° C.
Washings
3,5-minute washings in a washing buffer are carried out.
Deposit of the corresponding anti-immunoglobulin marked with peroxidase.
This reagent, diluted to ⅕00th, is deposited at a rate of 100 µl per cell. The mixture is then incubated for 30 minutes at 37° C.
Washings
5 5-minute washings in a washing buffer are carried out.
Revealing the peroxidase activity
200 µl of reagent (1 mg ABTS in 12 ml of 50 mM citrate buffer, pH 4, with 5/I of 30 vol. hydrogen peroxide added to it) is put in each cell and the preparations are incubated for 30 minutes at ambient temperature.
Reading
A spectrophotometer is used at 414 nm (green coloration).
b) Results
The differences obtained between the optical density averages of the negative and positive sera (under indirect immunofluorescence) allow infections with *L. infantum* to be revealed (see Table 12).

TABLE 12

|  | Negative sera | Positive sera |
| --- | --- | --- |
| Supernatant 6 days | 0.128 + 0.025 | 0.313 + 0.035 |
| Supernatant 15 days | 0.080 + 0.012 | 0.293 + 0.020 |
| Supernatant 21 days | 0.062 + 0.010 | 0.257 = 0.039 |

EXAMPLE 18

Production of the Excretion/Secretion Antigens from the Culture Supernatants Metabolized by the Different Parasitic Stages of *Leishmania*

The supernatants metabolized by the parasites of aseric culture, obtained at different times during the culture, are separated from the promastigote or amastigote forms by centrifugation then filtration on a 0.22 µm Millipore membrane treated beforehand with bacitracin (1 mg/ml). The sample is then concentrated by ultrafiltration on Mini Ultrassette (Filtron, cut-off threshold: 3 kDa), dialyzed overnight against distilled water and finally lyophilized. This process allows the culture supernatants to be concentrated more than 400 times.

The protein assays are carried out by spectrophotometry at 595 nm according to the Bradford method (Biorad Protein Assay Kit II). According to the species of *Leishmania*, from 1 to 4 µg antigen protein equivalent is thus obtained per ml of non-concentrated supernatant.

Biochemical and immunological characterizations of the excretion/secretion antigens of *L. infantum* and *L. amazonensis*:

The parasitic exoantigens are soluble molecules naturally released in the blood of the infected hosts and in the supernatants of in vitro cultures of these parasites. A distinction must be made between the true exoantigens (AES) resulting from the metabolism of the parasites, and the antigens resulting from their natural or artificial lysis.

According to the invention, incorporation of methionine $^{35}$S (1.85 MBq) is carried out from the third day (start of the exponential phase) of the culture of promastigote forms of *L. amazonensis* (MHOM/FE/16/JAP-78: diffuse cutaneous leishmaniasis) and of *L. infantum* (MOHM/MA/67/IT-263 clone 2: human visceral leishmaniasis) inoculated at a rate of 5×10$^5$ parasites/ml in a synthetic medium free from macromolecules. The AES's and the total parasitic polypeptide extracts (TPE) are analyzed using SDS-PAGE (10% polyacrylamide), under non-reducing conditions.

The kinetics of the incorporation of [$^{35}$ S]-methionine by the total or excretion/secretion proteins of *L. infantum* and *L. amazonensis* are respectively reported in FIGS. 11 and 12.

In FIGS. 11, A to D correspond to the total proteins extracted 24 hrs (A), 48 hrs (B), 72 hrs (C) and 96 hrs (D) after the addition of [$^{35}$ S]-methionine; E to H correspond to excreted/secreted proteins removed 24 hrs (E), 48 hrs (F), 72 hrs (G) and 96 hrs (H) after the addition of [$^{35}$S]-methionine.

In FIG. 12, A to D correspond to the total proteins extracted 24 hrs (A), 48 hrs (B), 72 hrs (C) and 96 hrs (D) after the addition of [$^{35}$ S]-methionine; E to H correspond to the excreted/secreted proteins removed 24 hrs (E), 48 hrs (F), 72 hrs (G) and 96 hrs (H) after the addition of [$^{35}$S]-methionine.

The radiolabelled profiles of the AES's are much less complex than those of the TPE's whatever the species studied. Only 16 excretion-secretion proteins are revealed both for *L. infantum* and for *L. amazonensis*.

Immunoprecipitations (IP) were carried out:
with sera of human or canine natural infections vis-á-vis the AES's and the TPE's (6 days of culture) of *L. infantum*
with sera of the experimental infestation of hamsters vis-á-vis the AES's and TPE's (6 days of culture) of *L. amazonensis*
with rabbit immunization sera vis-á-vis the AES's and PE's (6 days of culture) of *L. amazonensis*.

The results demonstrate immunogenicity of the AES's during natural or experimental infections. For the two parasites, certain antigens are recognized only at the level of the TPE's whilst others are peculiar to the AES's. For *L. infantum*, a similar humoral response is observed for 5 of the 6 human sera studied (2 doublets at about 70 kDa and about 45 kDa) vis-á-vis the AES's and the PE's; the dog serum recognizes different antigens (major antigens at about 90 and 66 kDa). For the hamster, an evolution of the humoral response exists vis-á-vis the AES's of *L. amazonensis* during the experimental infection. The antigens recognized at the time of an experimental or natural infection are different from those which are immuno-precipitated by an anti-TPE immunization serum in rabbits.

These results show that the AES's are capable of inducing an antibody response during infection by *L. amazonensis* and *L. infantum*. Taking account of their immunogenicity, the AES's constitute very useful tools with regard to leishmaniases in the domains of diagnostics and vaccination.

EXAMPLE 19

Production of Monoclonal Antibodies Against Excretion/Secretion Antigens of *L. amazonensis*.

Protocol Used
Immunization

2 μg of antigen (supernatant of aseric culture metabolized by promastigote forms at the end of the exponential phase of *L. amazonensis*, concentrated 200 times and dialyzed) is injected by sub-cutaneous route into the pad of the rear paw. The antigen preparation injected is called hereafter "Ag".

A protocol for rapid immunization of a BALB/c mouse is carried out as follows: $D_{-10}$: Ag+Freund's complete adjuvant (FCA) (V/V); $D_{-7}$ and $D_{-4}$: Ag+FIA; $Db_0$: recovery of the cells of the popliteal ganglia draining the rear paw.

Fusion

The myelomatous cells (X 63) are fused ($D_0$) with the lymphocyte cells in a ½ ratio in the presence of polyethylene glycol 4000 (50% PEG).

Screening

On $D_{+7}$, 442 wells (38%) had at least one cellular clone developing and 66 (5.7%) had confluent cells. The supernatants of the confluent cells are tested either by indirect immunofluorescence (IIF), or by the ELISA test. 19 of them were revealed to be positive using IIF, 9 using ELISA and 7 in both tests. In total, more than 1000 wells were screened. In 96-well dishes, in 24-well dishes and in 25 cm² dishes, 120, 47 and 36 hydridomas respectively were revealed to be secreting (revealed by IIF).

Cloning

The characteristic secreting hybridomas were cloned by limited dilution, 4 clones were the subject of a particular study (B3, C7, D9 and F5).

The results obtained are given in Table 13.

TABLE 13

| Strains/ascites | IB5/B3 | IIAIC7 | IVD4/D9 | IVD6/F5 |
| --- | --- | --- | --- | --- |
| *L. infantum* promastigotes | − | ± | − | + |
| *L. amazonensis* promastigotes | ++(1/10) | +(1/100) | +(1/1000) | +++(1/1000) |
| *L. amazonensis* amastigotes | + | − | + | + |
| *T. cruzi* | +/− | − | − | − |
| Molecular targets | 32 and | 32 and | between 30 | 60 kDa and |

TABLE 13-continued

| Strains/ascites | IB5/B3 | IIAIC7 | IVD4/D9 | IVD6/F5 |
| --- | --- | --- | --- | --- |
| under immuno-precipitation or Blotting | 50 kDa | 50 kDa | and 36 kDa | 45 kDa |

EXAMPLE 20

Obtaining Amastigote Forms Resistant to a Medicament

Promastigote forms of *L. mexicana* resistant to pentamidine are obtained by medicamentous pressure in vitro and have a resistance index of about 30. They are then transformed according to the culture method already described into corresponding cultured amastigote forms which, after determination of the IC50, retain the resistance to pentamidine induced in the promastigote forms.

FIG. 13 gives the variation in the percentage of growth relative to a control without drugs as a function of the concentration of pentamidine in μmole/l (curve □ corresponds to the untreated promastigote forms of *L. mexicana*, curve ♦ corresponds to the resistant promastigote forms and curve □ corresponds to the resistant amastigote forms. (IC50: concentration of pentamidine for which a growth inhibition of 50% is observed): IC50 untreated 1.2±0.05 μM IC50 resistant amastigote 32±1 μM and IC50 resistant promastigote 33 μM. The resistance index is equal to IC50 of the resistant strain/IC50 of the untreated strain. For the promastigotes the value is 27 and for the amastigotes it is 26.

Due to the production of the development cycle in vitro, the invention produces amastigote forms of *Leishmania* which are resistant to a medicament. This new experimental model allows the mechanism(s) involved in the induction of chemical resistance in the parasitic stage present in the infected host to be very closely studied.

The invention claimed is:

1. A non-infectious immunogenic composition comprised of an excretion or secretion antigen of about 55.4 kD as measured on SDS gel under non-reducing conditions, said antigen being isolated from culture supernatant conditioned by amastigote forms or promastigote forms of a parasite selected from the group consisting of *Leishmania infantum* and *L. chagasi* from an axenic culture devoid of serum, at exponential and/or stationary phases of their growth, in combination with a vehicle for delivery.

2. The composition of claim 1, in lyophilized form.

3. The composition of claim 1, wherein the vehicle is muramyldipeptide or saponin.

4. The composition of claim 1, further comprising a cytokine.

5. The composition of claim 4, wherein said cytokine is gamma interferon.

6. The composition of claim 1, wherein the parasite is *L. infantum*.

7. The composition of claim 1, wherein the parasite is *L. chagasi*.

8. The composition of claim 1, further comprising an adjuvant.

9. A non-infectious immunogenic composition comprised of an excretion or secretion antigen of about 55.4 kD as measured on SDS gel under non-reducing conditions, said antigen being isolated from culture supernatant conditioned by amastigote forms or promastigote forms of a parasite selected from the group consisting of *Leishmania infantum* and *L. chagasi* at exponential and/or stationary phases of their growth, free from any cellular and serum contaminants, as well as of molecules non-dialyzable at a cut-off threshold of 3 kDa, in combination with a vehicle.

10. The composition of claim 9, further comprising an adjuvant.

11. A method of immunization, said method comprising administration of the composition of claim 1 to a human or animal such that a specific immune response is elicited.

12. A method of immunization, said method comprising administration of the composition of claim 9 to a human or animal such that a specific immune response is elicited.

13. A method of obtaining the composition of claim 1, said method comprising:

(a) isolation of an excretion or secretion antigen of about 55.4 kD as measured on SDS gel under non-reducing conditions from a culture supernatant conditioned by amastigote forms or promastigote forms of a parasite selected from the group consisting of *Leishmania infantum* and *L. chagasi* from an axenic culture devoid of serum, at exponential and/or stationary phases of their growth and (b) combining said antigen with a vehicle for delivery.

14. A method of obtaining the composition of claim 9, said method comprising:

(a) isolation of an excretion or secretion antigen of about 55.4 kD as measured on SDS gel under non-reducing conditions from a culture supernatant conditioned by amastigote forms or promastigote forms of a parasite selected from the group consisting of *Leishmania* infantum and *L. chagasi* at exponential and/or stationary phases of their growth, free from any cellular and serum contaminants, as well as of molecules non-dialyzable at a cut-off threshold of 3 kDa and (b) combining said antigen with a vehicle.

* * * * *